US008277388B2

(12) United States Patent
Muramatsu et al.

(10) Patent No.: US 8,277,388 B2
(45) Date of Patent: Oct. 2, 2012

(54) BLOOD RHEOLOGY MEASURING APPARATUS

(75) Inventors: Hiroyuki Muramatsu, Chiba (JP);
Takahiko Nakamura, Chiba (JP);
Minao Yamamoto, Chiba (JP);
Masataka Shinogi, Chiba (JP)

(73) Assignee: Seiko Instruments Inc. (JP)

( * ) Notice: Subject to any disclaimer, the term of this patent is extended or adjusted under 35 U.S.C. 154(b) by 1714 days.

(21) Appl. No.: 11/602,374

(22) Filed: Nov. 20, 2006

(65) Prior Publication Data

US 2007/0191720 A1 Aug. 16, 2007

Related U.S. Application Data

(62) Division of application No. 10/190,783, filed on Jul. 8, 2002, now Pat. No. 7,147,602.

(30) Foreign Application Priority Data

| Jul. 9, 2001 | (JP) | 2001-208397 |
| Aug. 21, 2001 | (JP) | 2001-250361 |
| Sep. 13, 2001 | (JP) | 2001-278385 |
| Dec. 17, 2001 | (JP) | 2001-382909 |

(51) Int. Cl.
*A61B 5/026* (2006.01)
*A61B 8/06* (2006.01)

(52) U.S. Cl. ........................ 600/504; 600/454
(58) Field of Classification Search .......... 600/504–507, 600/453–457
See application file for complete search history.

(56) References Cited

U.S. PATENT DOCUMENTS

| 4,425,922 | A | * | 1/1984 | Conti et al. | 600/504 |
| 5,080,106 | A | * | 1/1992 | Sekii et al. | 600/505 |
| 5,779,641 | A | * | 7/1998 | Hatfield et al. | 600/443 |
| 5,899,863 | A | * | 5/1999 | Hatfield et al. | 600/443 |
| 5,904,653 | A | * | 5/1999 | Hatfield et al. | 600/454 |
| 5,954,653 | A | * | 9/1999 | Hatfield et al. | 600/443 |
| 5,971,927 | A | * | 10/1999 | Mine | 600/455 |
| 5,983,120 | A | * | 11/1999 | Groner et al. | 600/310 |
| 6,030,344 | A | * | 2/2000 | Guracar et al. | 600/447 |
| 6,086,539 | A | * | 7/2000 | Guracar et al. | 600/453 |
| 6,093,149 | A | * | 7/2000 | Guracar et al. | 600/447 |
| 6,106,477 | A | * | 8/2000 | Miesel et al. | 600/486 |
| 6,110,118 | A | * | 8/2000 | Guracar et al. | 600/453 |
| 6,193,664 | B1 | * | 2/2001 | Guracar et al. | 600/453 |
| 6,241,677 | B1 | * | 6/2001 | Guracar et al. | 600/453 |
| 6,258,029 | B1 | * | 7/2001 | Guracar et al. | 600/443 |
| 6,261,244 | B1 | * | 7/2001 | Kensey et al. | 600/573 |
| 6,280,387 | B1 | * | 8/2001 | Deforge et al. | 600/454 |
| 6,319,205 | B1 | * | 11/2001 | Goor et al. | 600/485 |
| 6,322,509 | B1 | * | 11/2001 | Pan et al. | 600/443 |
| 6,322,511 | B1 | * | 11/2001 | Guracar et al. | 600/453 |

(Continued)

*Primary Examiner* — Navin Natnithithadha
(74) *Attorney, Agent, or Firm* — Adams & Wilks

(57) ABSTRACT

A blood rheology measuring apparatus has a measuring portion for measuring a flow velocity of the blood flowing in a blood vessel of a person in a mode of a Doppler shift signal by transmitting and receiving a wave to and from a surface of the person's skin. An information processing portion calculates an intensity at each of frequency components of the Doppler shift signal, extracts a maximum frequency in a signal at an intensity level equal to or larger than a threshold in the histogram or a maximum frequency when an integrated value from a low frequency component reaches a predetermined rate of a total thereof in the histogram, and provides a temporal change waveform of the extracted frequency. The blood rheology is analyzed by an area value of a portion at and above a line connecting a minimum value of one pulse waveform and a minimum value of a successive pulse waveform of the frequency waveform.

26 Claims, 27 Drawing Sheets

U.S. PATENT DOCUMENTS

| | | |
|---|---|---|
| 6,402,690 B1 * | 6/2002 | Rhee et al. ............... 600/300 |
| 6,464,640 B1 * | 10/2002 | Guracar et al. ............... 600/453 |
| 6,514,208 B1 * | 2/2003 | Cancio et al. ............... 600/454 |
| 6,554,774 B1 * | 4/2003 | Miele ............... 600/485 |
| 7,147,602 B2 * | 12/2006 | Muramatsu et al. ............... 600/504 |
| 7,959,575 B2 * | 6/2011 | Muramatsu et al. ............... 600/504 |
| 2003/0171667 A1 * | 9/2003 | Seward ............... 600/407 |

* cited by examiner

| | SUBJECT A | SUBJECT B | SUBJECT C | SUBJECT D | SUBJECT E |
|---|---|---|---|---|---|
| BEFORE MEAL | ○ | ☆ | ◇ | □ | △ |
| AFTER MEAL | ● | ★ | ◆ | ■ | ▲ |

A

B

BLOOD RHEOLOGY MEASURING APPARATUS

CROSS REFERENCE TO RELATED APPLICATION

The present application is a division of prior U.S. application Ser. No. 10/190,783, filed on Jul. 8, 2002, now U.S. Pat. No. 7,147,602, which is hereby incorporated by reference, and priority thereto for common subject matter is hereby claimed.

BACKGROUND OF THE INVENTION

1. Field of the Invention

The present invention relates to a blood rheology measuring apparatus indicating a flowability referred to generally as a fluent/viscous degree of blood, particularly to a technology of measuring an amount of a blood flow flowing in the artery, discerning a very small circulating blood flow rate constituting a basis of activity of the human texture and carrying out assessment of health, diagnosis of disease, assessment of effect of medicine and the like.

2. Description of the Related Art

It has conventionally been carried out to measure blood rheology for carrying-out assessment of health of human being, diagnosis of disease, assessment of effect of medicine on the human body, assessment of soundness and functional performance of food or the like, and carrying out the assessment and the diagnosis from a result thereof. As a conventional technology, there is known a method presented by Yuji Kikuchi under a title of "Measurement of total blood flowability using a capillary model" in a professional magazine "Food research result information, No. 11 issued in 1999", that is, a method of sampling blood from a subject, using a micro-channel array fabricated by a lithographic method and measuring blood rheology from a pass time period of blood under constant pressure.

According to the method, first, the elbow of the subject is disinfected by alcohol cotton and blood is sampled from the elbow vein by using a vacuum blood sampling tube in which there is put a heparin solution to constitute a quantity of 5% as an anticoagulant by using a 1 ml disposable syringe and a 23G disposable needle before sampling blood. Next, there are prepared micro-channels of a capillary model fabricated by a silicon chip (micro-channel array silicon chip), which are aligned in parallel with each other by 8736 pieces with a size of a width of 7 µm, a length of 30 µm and a depth of 4.5 µm, subjected to ultrasonic cleaning in a pertinent amount of mixture solution of distilled water, ethanol and a liquid neutral detergent (trade name: mamalemon) (aiming 1:1:0.3) and sets to a blood rheology measuring apparatus (MC-FAN). Further, after cleaning a cylinder for a sample in the apparatus by distilled water, physiological salt water is substituted therefor and micro-channel array pass time period is measured by a difference of 20 cmAq by using 100 µl of the physiological salt water.

After measuring the physiological salt water, blood is measured. First, 200 through 300 µl of a blood sample is sampled by using the 1 ml disposable syringe attached with the 23G disposable needle and further attached with about 10 cm of a polyethylene tube at a needle tip thereof, a tip of the polyethylene tube is put to the bottom of the cylinder and the blood sample is injected to push up the remaining physiological salt water. Further, the blood sample is controlled to constitute 100 µl while extracting blood from an upper end opening portion of the cylinder by using the polyethylene tube and a micro-channel array pass time period of 100 µl of blood is measured by a difference of 20 cmAq. similar to the case of the physiological salt water.

With regard to the micro-channel array pass time periods of the physiological salt water and the sampled blood calculated in this way, the pass time period of the sampled blood is corrected by the pas pass time period of the physiological salt water and the time period is defined as a total blood pass time period to constitute an index of blood rheology. For example, when the total blood pass time period is short, blood rheology is low and therefore, the blood flows in the capillary tube without resistance. That is, there is increased the very small circulating blood flow amount constituting the basis of activity of the human texture and therefore, the total blood pass time period can certify the healthy body.

However, according to the conventional blood rheology measuring method using the micro-channel array, blood needs to sample by piercing the elbow by using the injection needle in order to sample blood from the subject. Therefore, in carrying out an in-vivo test for examining influence of a food component on blood rheology, blood cannot be sampled from same person for many times in a day and there poses a problem that a continuous test is difficult. Further, even when an individual intends to measure blood rheology by sampling blood by oneself at one's own house apart from a medical institution, according to a method of using a micro-channel array as in the conventional example, the apparatus cannot be put in one's own house, a pertinent treatment cannot be carried out and therefore, there also poses a problem that blood rheology can be measured only at a medical institution.

It is an aspect of the present invention to provide a noninvasive blood rheology measuring apparatus, which is also a small-sized and portable apparatus, capable of simply and conveniently measuring blood rheology information without sampling blood from a subject when measuring blood rheology and means for enabling to measure blood rheology at any time, at anywhere and simply even at other than a medical institution without applying burden on the subject.

SUMMARY OF THE INVENTION

A blood rheology measuring apparatus according to the invention is on the basis of a constitution comprising means for noninvasively detecting a flow velocity of the blood flowing in the blood vessel as a Doppler shift signal by transmitting and receiving a wave from a face of the skin and means for analyzing blood rheology from a temporal change of a value of the flow velocity of the blood detected by the means and the apparatus is small-sized, portable and capable of simply measuring blood rheology at any time at anywhere even at outside of a medical institution without applying burden on a subject.

Hence, according to an aspect of the invention, there is provided a blood rheology measuring apparatus comprising a measuring portion for measuring information with regard to blood circulation at inside of a living body from a surface of the living body, and a signal processing portion for processing a signal detected from the measuring portion, wherein information with regard to a blood rheology is provided as a result of processing the signal.

Further, the measuring portion and the signal processing portion are integrally or separately made portable to thereby enable to provide the information with regard to the blood rheology continuously or daily. Further, the information with regard to the blood circulation to be measured in the measuring portion is a change in a blood flow velocity based on a Doppler effect by a blood flow. The measuring portion is an ultrasonic wave sensor for transmitting and receiving an ultrasonic wave.

Further, the measuring portion is constructed by a constitution constituting a sensor for detecting information with regard to a pulse wave or a constitution having an input device for inputting individual information of gender or the like of a person to be measured for correcting measured data.

As a result of the signal processing, information with regard to life habit suitable for the person to be measured is informed to a subject based on a result of measuring the blood rheology of the person to be measured or there is provided a data holding portion for storing information with regard to the measured blood rheology to thereby enable to hold daily blood rheology information of the person to be measured.

Further, the measuring portion is constructed a constitution integrated to a blood pressure meter or a pulse meter and capable of being utilized in measuring blood pressure or measuring pulse.

Further, there is provided inputting means for inputting daily eating habit information of the person to be measured and there is provided determining means for determining whether the eating habit of the person to be measured is suitable for the person to be measured from the information with regard to the blood rheology to thereby enable to inform a result of determination by the determining means to the person to be measured.

Further, for correcting the information with regard to the measured blood rheology, there is constructed a constitution having a temperature measuring portion brought into contact with a surface of the living body for measuring temperature of inside or the surface of the living body at a vicinity of the measuring portion or the measuring portion generates heat in measuring to thereby elevate a temperature of the measuring portion.

Further, the measuring portion is constructed by a constitution held by a holding portion capable of holding the measuring portion by bringing the measuring portion into contact with the surface of the living body or a constitution in which the measuring portion and the temperature measuring portion are blocked from outside air, or the holding portion is constituted by a member having insulating performance or a member having elasticity such as rubber. Further, a shape of the holding portion is constituted by a shape of a finger ring or a shape of a mouse.

Further, in analyzing the blood rheology from the temporal change of the flow velocity value of the blood, there is constructed (1) a constitution utilizing a maximum blood flow velocity for one pulse, (2) a constitution dividing the maximum blood flow velocity for one pulse by an integrated value of a pulse velocity, (3) a constitution for providing a Doppler shift intensity waveform reflected and returned from blood flow, calculating an intensity of each of frequency components of the Doppler shift signal (histogram), extracting a maximum frequency in a signal at an intensity level equal to or larger than a threshold in the histogram or a maximum frequency when an integrated value from a lower frequency component reaches a predetermined rate of a total thereof in the histogram, providing a waveform of a temporal change of the extracted frequency (frequency waveform) and analyzing blood rheology based on the maximum frequency in the frequency waveform, or (4) a constitution for analyzing blood rheology by an area value of a portion at and above a line connecting a minimum value of a one pulse waveform and a minimum value of a successive pulse waveform of the frequency waveform.

Further, the means for noninvasively detecting the flow velocity of the blood flowing in the blood vessel includes a constitution of adopting an ultrasonic wave transmitter and receiver for transmitting and receiving an ultrasonic wave to and from the artery of the finger portion, or a constitution for adopting an ultrasonic wave transmitter and receiver for transmitting and receiving an ultrasonic wave to and from the artery at the finger tip portion.

Further, according to another aspect of the invention, there is provided a blood rheology measuring apparatus including a compensating function by providing (1) means for operating and compensating for an amount of a change in the flow velocity of the blood based on expansion and construction of the blood vessel by a temperature value detected by means for detecting temperature of the blood vessel portion for detecting the blood flow and comprising (2) means for operating and compensating for an amount of a change based on blood pressure by dividing by a blood pressure value detected by blood pressure measuring means.

BRIEF DESCRIPTION OF THE DRAWINGS

FIGS. 6A and 6B are explanatory views of Embodiment 1 (Embodiment 2) according to the invention in which FIG. 6A shows a finger ring type blood rheology measuring apparatus mounted to the finger and FIG. 6B illustrates a section taken along a line A-A' of FIG. 6A;

FIG. 15A is an outlook view of a wrist watch type blood rheology measuring apparatus constituting a fifth embodiment of the invention and FIG. 5B is a view showing a measuring state of the wrist watch type blood rheology measuring apparatus;

DETAILED DESCRIPTION OF THE PREFERRED EMBODIMENTS

Figure 1:
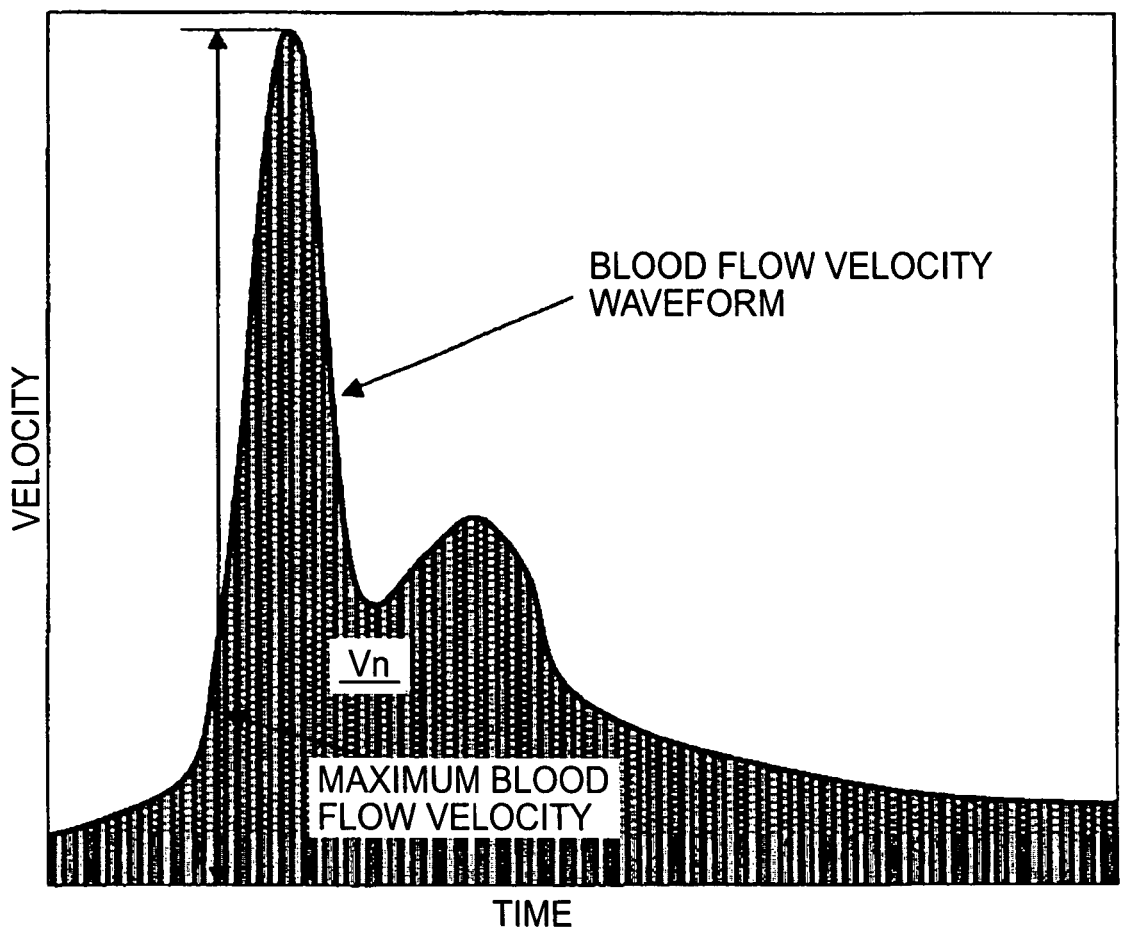
FIG. 1 is a diagram for explaining a first blood rheology analyzing method according to the invention.

The blood rheology, that is, the flowability of blood is brought into a close relationship with a viscosity of blood and when a change in a blood flow velocity is large, it can be regarded that there is brought about a state of low viscosity of blood. According to the conventional measuring method, the viscosity is measured by the time period by which a predetermined amount of blood passes through the micro-channel array by a predetermined water column pressure difference and the time period is compared with that of the physiological salt water constituting a reference, which basically constitutes measurement of the viscosity. It is deduced that when blood is fluent, the blood is to flow excellently at inside of the blood vessel and blood flow is continued even at timings at which delivering pressure is not operated in the pumping action of the heart. The measurement principle of the blood rheology measuring apparatus according to the invention is based on the knowledge that there is a correlation between a form of a temporal change of a blood flow velocity appearing in pulsing with rheology of blood for calculating blood rheology from a change in the blood flow velocity appearing in pulsation.

Further, the blood rheology measuring apparatus of the invention comprises means for noninvasively detecting the flow velocity of blood flowing in the blood vessel as a Doppler shift signal by transmitting and receiving a wave to and from the skin face and means for analyzing a blood rheology from a change over time of a value of the blood flow velocity detected by the means as its basic constitution. A wave signal having a constant frequency radiated from the skin face to inside of the body, is returned by being reflected by a substance in the body. By receiving a reflected wave signal thereof, the flow velocity of blood flowing in the blood vessel included therein is detected and a reflecting substance is not specified to the blood flow in the blood vessel. In the case of the blood flow in the blood vessel, the blood flow is moved with a velocity component and therefore, according to a reflected wave thereof, a frequency of wave is shifted by the Doppler's effect, however, in the case of a stationary substance which is not provided with a velocity component, such as bone or the blood vessel, the wave is reflected and returned to stay with the constant frequency.

Further, there are present not only blood in the blood vessel, to which attention is paid as a substance having a velocity component but also various substances such as blood or lymph in the capillary directed in various directions and reflected waves from these are superposed on a received wave. A component the same as that of the frequency on a transmitting side is reflected from a stationary substance and therefore, the component can easily be removed. A physical amount intended to detect in the invention is a flow velocity of blood in the blood vessel to which attention is paid and generally a signal having the highest level as the frequency component corresponds to an average flow velocity of flow of blood in the blood vessel and therefore, the component is extracted. In detecting the flow velocity of blood, the technology of the conventional ultrasonic blood flow meter is applicable as it is. Further, although ultrasonic wave is generally used for a wave used in detecting the blood flow velocity, other wave of laser or the like can also be used. Further, a pulse waveform is one of indexes indicating a blood circulating dynamic state and it seems that by measuring a rise velocity of the pulse waveform or measuring a velocity of changing a diameter of the blood vessel, a correlation thereof with blood rheology can be obtained.

An explanation will be given of a method of analyzing blood rheology from a temporal change of a blood flow velocity value detected in the invention as follows. FIG. 1 shows a graph of a temporal change of a blood flow velocity in accordance with pulsing. As a characteristic component of blood rheology, by utilizing a maximum blood flow velocity Vx, the inventors have been able to confirm a correlation thereof with blood rheology and have acquired knowledge that even a ratio Vn of Vx as compared with a pulse velocity waveform, the ratio has a correlation with blood rheology. The ratio Vn is calculated by dividing the maximum blood flow velocity Vx by an integrated value of the pulse velocity waveform (an integrated value of the pulse velocity waveform in one period of pulse: a pattern portion in the drawing). This is a first method of analyzing blood rheology according to the invention.

$$Vn = C \times Vx / (\text{integrated value of pulse velocity waveform}) \quad (1)$$

where notation C designates a correction coefficient. The apparatus of the invention carries out an in-vivo measurement, the measured blood flow velocity is not only dependent on blood rheology but also dependent on conditions such as thickness and wall quality of the blood vessel and blood pressure and therefore, although the blood flow velocity information can relatively measure blood rheology, the blood flow velocity information cannot absolutely measure blood rheology. Hence, it is necessary as the premise of measurement of the invention to acquire a correction amount in correspondence with an absolute value by carrying out a correction in parallel with measurement by the conventional method capable of carrying out the absolute measurement by comparing with a reference of physiological salt water or the like and the method of the invention. Further, it has been confirmed that even by utilizing the maximum blood flow velocity Vx without carrying out the correction of Equation (1), there is established the correlation with blood rheology.

Figure 2:
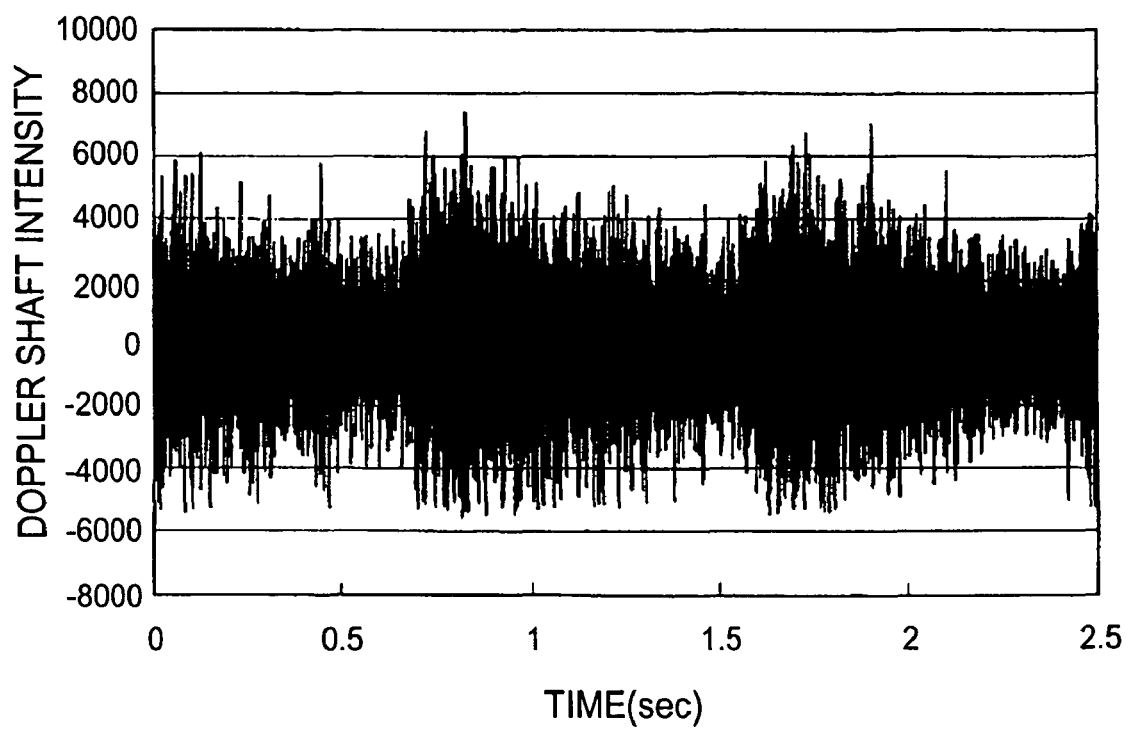
FIG. 2 is a diagram showing a Doppler shift intensity waveform of a signal received by an ultrasonic receiver according to the invention.

Next, an explanation will be given of a second method of analyzing blood rheology according to the invention. There is arranged an ultrasonic sensor paired with an ultrasonic wave incident portion and an ultrasonic wave detecting portion to be opposed to the artery disposed proximately to the surface of the body and an ultrasonic wave is radiated toward the artery by exciting an ultrasonic wave transmitter of the ultrasonic wave incident portion by a constant frequency of about 9.6 MHz. In the ultrasonic wave detecting portion, the ultrasonic wave detecting portion receives an ultrasonic wave signal reflected to return by inside of the body. As described above, the received signal includes ultrasonic waves reflected by various portions at inside of the body, when a reflecting substance is stationary, a frequency of a reflected wave remains unchanged from the frequency of the incident wave and when the reflecting substance is a moving substance, the reflected wave is reflected by undergoing a frequency shift (Doppler shift) in accordance with a moving amount thereof. An intensity of the Doppler shift is extracted from the received signal to acquire a temporal procedure thereof. A waveform diagram of FIG. 2 indicates the temporal procedure and the temporal procedure is referred to as a Doppler shift intensity waveform. The Doppler shift intensity waveform is measured by using a sampling rate equal to or larger than 1/5000 of the frequency of the input waveform.

Specifically, when the Doppler shift intensity waveform is calculated, in the case of the input waveform frequency of 9.6 MHz, the sampling rate is made to be equal to or larger than 1.92 kHz. The reason is that when the sampling rate is less than 1.92 kHz, the frequency waveform cannot be reproduced from the Doppler shift intensity waveform. In the case of the input waveform frequency of 9.6 MHz, the Doppler shift intensity waveform sampled at 1.92 KHz or higher, can measure a frequency component of an intensity change of the Doppler shift intensity equal to or lower than 0.96 kHz at minimum. When the frequency waveform is calculated from the frequency component, rheology of a viscous can be calculated. According to the invention, by subjecting the Doppler shift intensity signal to high-speed Fourier transformation (FFT), there is calculated an intensity distribution (histogram) of a frequency indicating the periodicity.

Figure 3:
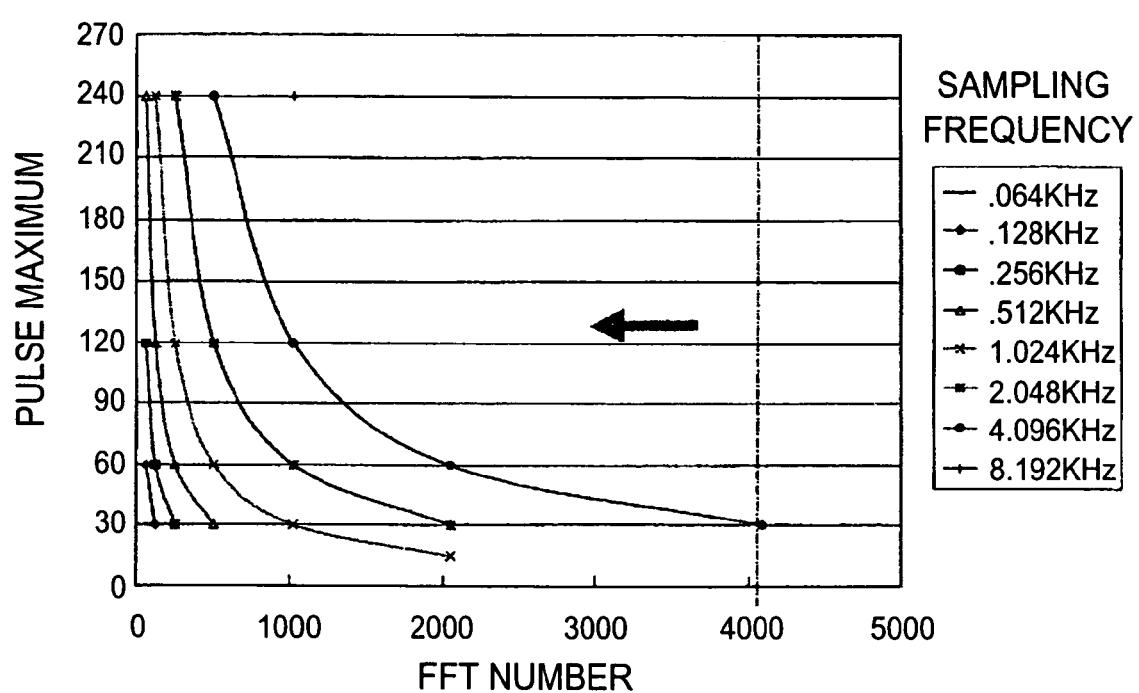
FIG. 3 is a graph showing a relationship between an FFT number in subjecting the Doppler shift intensity signal to high-velocity Fourier transformation and a pulse maximum sensitivity.

In order to analyze the frequency waveform, there is needed data at every 250 ms (8 Hz) at the latest. This is a rate when a maximum number of a pulse number is assumed to be 240 pulses (in correspondence with a pulse number in exercise) and normally, a temporal change of the frequency is analyzed by using data at every 23.22 ms. This is a rate sufficiently fast for 250 ms. Further, a relationship between the sampling rate for calculating the Doppler shift intensity waveform and a number of sampling data used in carrying out FFT, is brought into a close relationship with a pulse number of a person to be measured, for example, in considering a case of measuring a person pulsing at 60 pulses, when there is used a sampling frequency (1.92 kHz) constituting a limit capable of reproducing the Doppler intensity waveform, the frequency waveform in accordance with pulsing cannot be provided unless the number of FFT is made to be equal to or less than 1000. Further, when a maximum sensitivity of pulsing is increased to 90 pulses, 120 pulses, unless the number of FFT is reduced to 600, 500, the frequency waveform in accordance with pulsing cannot be provided. FIG. 3 is a graph showing the relationship. It has been confirmed that when the number of FFT is made to be about 256, the number is almost made regardless of increasing pulsation or increasing the sampling rate and therefore, generally, the number of FFT is made to be about 256.

According to the invention, there are adopted the following two methods as methods of calculating a frequency waveform from a frequency component. One of the methods is a threshold designating method and other thereof is a rate comparing method. First, with regard to the threshold designating method, the procedure is as follows.

(1) There is carried out FFT of a Doppler shift intensity signal to calculate a frequency component.
(2) A power spectrum value of a frequency calculated by FFET is compared with a certain threshold.
(3) Frequencies having power spectrum values larger than the threshold are sampled.
(4) A highest frequency in the sampled frequencies is selected as a frequency component for forming the frequency waveform. The highest frequency indicates a reflected wave from a reflecting substance in the body having the fastest moving speed and although there is a case that the reflected wave indicates motion of muscle or the like, generally, the reflected wave can be interpreted to correspond to a flow velocity of blood flowing in the artery to which attention is paid.
(5) The frequency waveform is formed by repeating operation of steps (1) through (4) for Doppler shift intensity signals at respective time points. Here, a temporal resolution of the frequency waveform is constituted by a product of the sampling rate of the Doppler shift intensity waveform by the FFT number.

Figure 4:
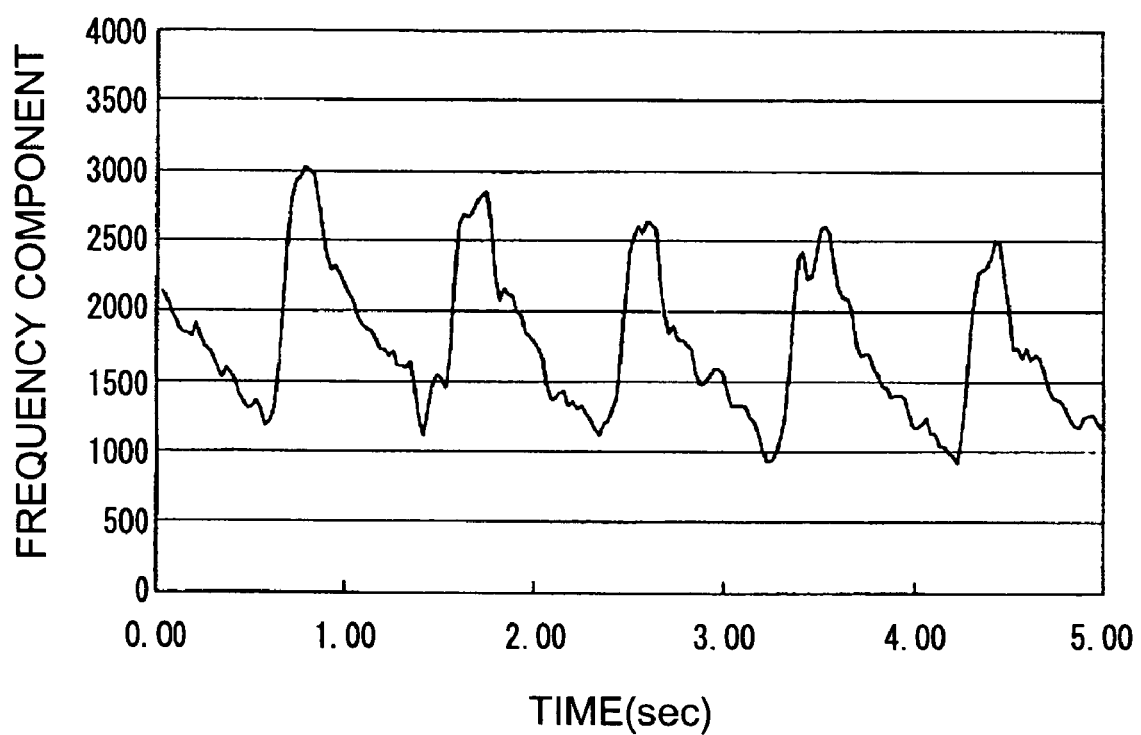
FIG. 4 is a diagram showing a frequency waveform according to the invention extracted from the Doppler shift intensity signal.

FIG. 4 shows a frequency waveform provided thereby. Generally, the frequency waveform is formed with 10000 as the threshold. The waveform is similar to the pulse waveform provided from blood flow velocity information (refer to FIG. 1).

Next, with regard to another method of calculating the frequency waveform from one frequency component, or the rate comparing method, the procedure is as follows.

(1) There is carried out FFT of a Doppler shift intensity waveform for calculating a frequency component.
(2) There is calculated a total of power spectrum values of frequencies calculated by FFT.
(3) The power spectrum values are added successively from power spectrum values having lower frequencies.
(4) The sum is divided by the total of the power spectrum values to thereby calculate a rate.
(5) The rate is compared with a certain set rate.
(6) A frequency having a power spectrum value added when the rate becomes larger than the set rate as a result of comparison, is selected as a frequency component for forming the frequency waveform.
(7) The frequency waveform is formed by repeating operation of steps (1) through (6) with regard to Doppler shift intensity signals at respective time points. Here, a temporal resolution of the frequency waveform is constituted by a product of the sampling rate of the Doppler shift intensity waveform by the FFT number.

There is provided a frequency waveform similar to that in FIG. 4 by such a procedure. The method is a method tried in view of the fact that the threshold designating method is liable to be effected by influence of high frequency noise and a high frequency region is abandoned to remove the high frequency noise. There is not an absolute significance in the rate set value in this case, generally, the frequency waveform is formed with 80% (0.8) as the rate set value. The frequency waveform by the method is difficult to be effected by influence of high frequency noise, on the other hand, the method is inferior to the threshold designating method in view of accuracy and therefore, the threshold designating method may be adopted by dealing with the high frequency noise by preventing unrealistic high frequency components from being picked up.

Figure 5:
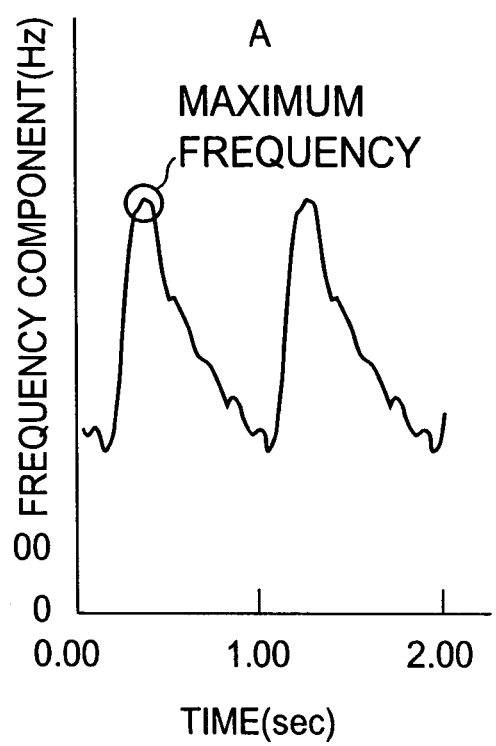
FIG. 5A is a diagram for explaining a second blood rheology analyzing method according to the invention extracted from a frequency waveform and FIG. 5B is a diagram for explaining a third blood rheology analyzing method according to the invention.
Figure 5:
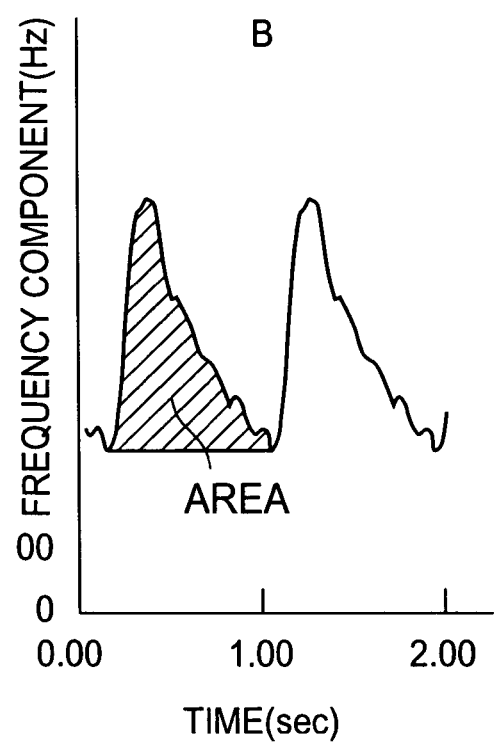

In the case of a second method of analyzing blood rheology according to the invention, as shown by FIG. 5A, a maximum frequency is specified in the provided frequency waveform and rheology is calculated by using the maximum frequency. The method is based on a prediction that when blood is fluent, blood flow is easy to flow and the maximum blood flow velocity is increased. Although generally, there is calculated an average of maximum frequency values of about three pulses; as shown by FIG. 4, there is a case in which the frequency waveform includes low frequency components and maximum frequencies at respective pulses vary. When the maximum frequency is shifted at respective pulse, sampling may be carried out at a long period of pulsing.

In the case of a third method of analyzing blood rheology according to the invention, a pulse waveform of one pulse is sampled from a frequency waveform and an area value thereof is calculated to thereby calculate rheology. The method is based on a prediction that when blood is fluent, even at timings at which delivery pressure by pumping action of the heart is not applied, blood is predicted to flow as it is by inertia force and therefore, an integrated value of one pulse will be increased. However, it is predicted that information at low flow velocity near to 0 includes not few other velocity information of the vein or the like and therefore, according to the invention, as shown by FIG. 5B, there is calculated an area of a portion at and above a line connecting a minimum value of a waveform of one pulse and a minimum value of a waveform of successive pulse.

Measurement of blood rheology according to the invention is based on information of blood flow at inside of the actual blood vessel in the body and therefore, the detected blood flow signal is varied by being effected with influence of expansion or contraction of the blood vessel based on body temperature or influence of blood pressure. That is, when the body temperature rises, the blood vessel is expanded to be thick, blood becomes easy to flow, blood flow velocity is increased, however, this is a factor irrelevant to blood rheology. Further, a variation in the blood pressure value corresponds to a change in pump pressure operated to a flow path and the flow velocity (blood flow velocity) is varied in accordance therewith. This is also a variation in blood flow based on a factor irrelevant to blood rheology. Hence, according to the invention, there is adopted a constitution in which these values are separately detected and amounts of variation based thereon are compensated for.

Embodiment 1

An explanation will be given of a blood rheology measuring apparatus according to an embodiment of the invention in reference to the attached drawings. The apparatus is constituted by the first blood rheology analyzing method according to the invention of calculating the ratio by dividing the maximum blood flow velocity Vx shown in FIG. 1 by an integrated value of a pulse velocity waveform (an integrated value of a pulse velocity waveform in one period of pulse). FIGS. 6A and 6B are views showing an outlook constitution of the embodiment of the blood rheology measuring apparatus used in the embodiment. As shown by FIG. 6A, the blood rheology measuring apparatus is constituted by being classified in two of a finger ring portion 1 and a signal processing portion 2.

Figure 6:
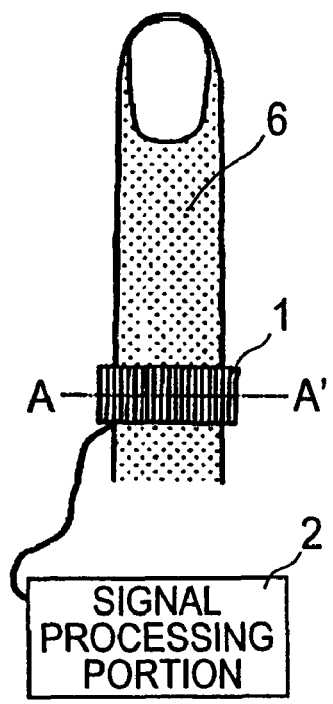
Figure 6:
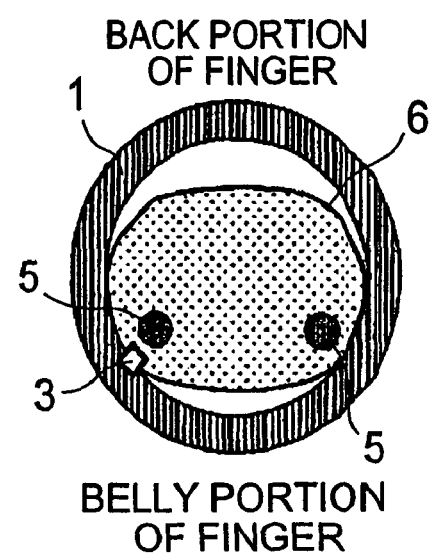
Figure 7:
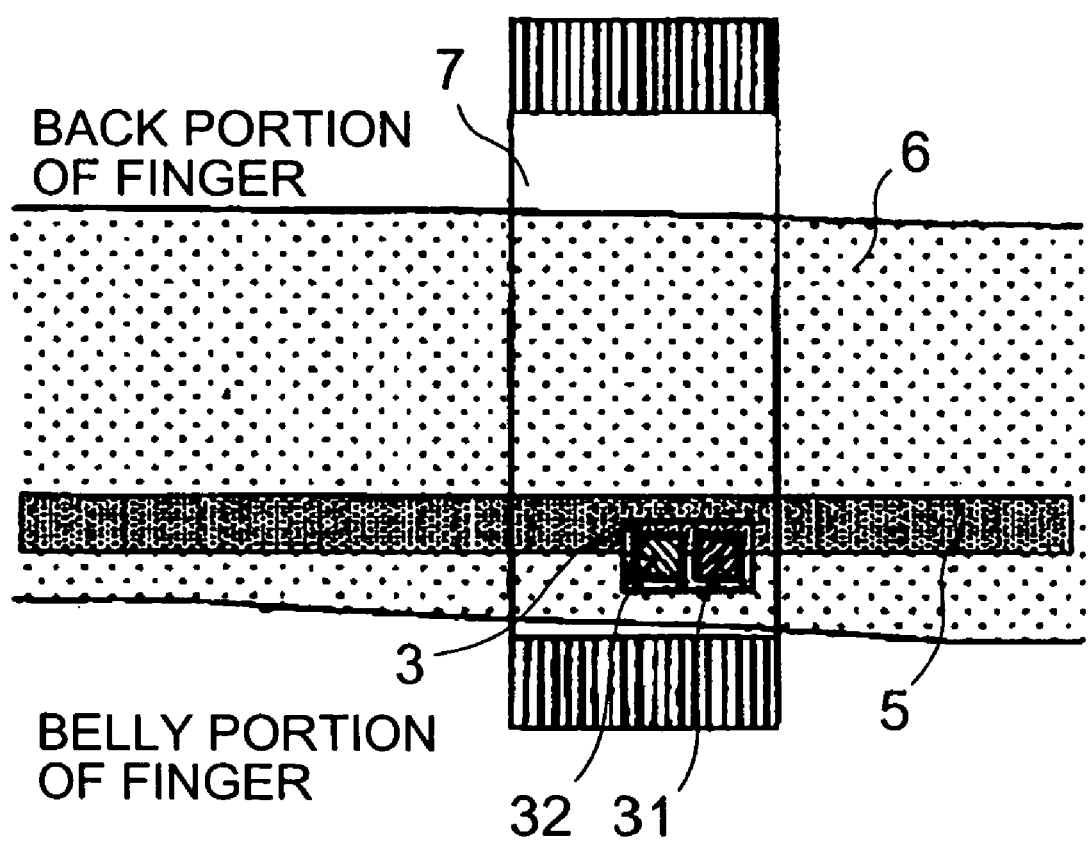
FIG. 7 is an explanatory view of Embodiment 1 according to the invention and is a perspective sectional view of inside of a finger ring viewing from a B direction shown in FIG. 6B.

FIG. 6B illustrates a section taken along a line A-A' of FIG. 6A with regard to Embodiment 1. As shown by FIG. 6B, an ultrasonic wave sensor portion 3 is present on an inner side of the finger ring portion 1. FIG. 7 shows a sectional view of inside of the finger ring viewed from a B direction shown in FIG. 6B. In the ultrasonic sensor portion 3, an ultrasonic wave incident portion 31 and an ultrasonic wave detecting portion 32 are attached at a belly portion of the finger 6. Further, the arteries 5 disposed in the finger 6 are extended to the finger tip by passing both sides of the belly portion of the finger 6 and therefore, in order to measure flow of blood of the artery, the ultrasonic wave incident portion 31 and the ultrasonic wave detecting portion 32 are attached to a portion of the finger 6 shifted to the left of the center of the belly as shown by FIG. 6B such that an ultrasonic wave can be incident to aim at the artery. Thereby, reflection from the artery, can firmly be caught and accuracy of measuring blood flow is promoted. Although the portions 31 and 32 are attached to shift to the left, even when the portions 31 and 32 are attached to shift to the right to aim at the artery on the right side, the effect stays the same.

The blood rheology measuring apparatus of Embodiment 1 is normally portable by mounting the finger ring portion 1 on the finger 6 and mounting the signal processing portion 2 on the arm. Further, also the signal processing portion 2 may be mounted on the finger 6 similar to the finger ring portion 1. The signal processing portion 2 and the ultrasonic wave incident portion 31 and the ultrasonic wave detecting portion 32 installed at the finger ring portion 1, are connected by lead wires, a driving voltage signal is inputted from the signal processing portion 2 to the ultrasonic wave incident portion 31 via the lead wire and at the ultrasonic wave detecting portion 32, a measured voltage signal is inputted to the signal processing portion 2.

Figure 8:
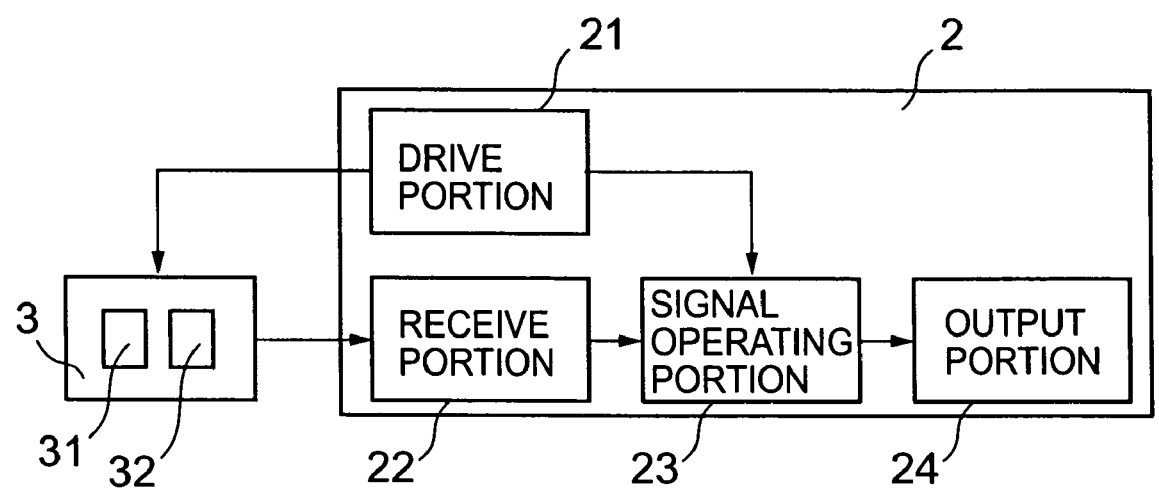
FIG. 8 is a block diagram showing an inner constitution of a signal processing portion of a blood rheology measuring apparatus of Embodiment 1 (Embodiments 3, 4, 5) and a state of connecting the signal processing portion and an ultrasonic sensor portion at inside of a finger ring portion.

FIG. 8 shows a block diagram showing an inner constitution of the signal processing portion 2 of the blood rheology measuring apparatus according to Embodiment 1 and a state of connecting the signal processing portion 2 and the ultrasonic wave sensor portion 3 at inside of the finger ring portion 1. As illustrated, the signal processing portion 2 is generally constituted by a drive portion 21, a receive portion 22, a signal operating portion 23 and an output portion 24. The drive portion 21 of Embodiment 1 oscillates PZT installed at the ultrasonic incident portion 31 and transmits drive voltage for making an ultrasonic wave incident on the artery 5. The receive portion 22 receives voltage generated when PZT installed at the ultrasonic wave detecting portion 32 receives the ultrasonic wave.

The signal operating portion 23 carries out various processings with regard to measurement of blood rheology by executing processing programs stored to a storage region (illustration is omitted) provided at inside thereof and outputs a result of the processings to the output portion 24. Further, the signal operating portion 23 calculates the Doppler effect of blood flow by comparing a frequency of the ultrasonic wave emitted from the ultrasonic wave incident portion 31 and a frequency of the ultrasonic wave received by the ultrasonic wave detecting portion 32. Further, the signal operating portion 23 calculates a flow velocity of blood flowing in the artery 6 by a change in the frequency and calculates a temporal change of the velocity. Further, there is a correlation between the form of the temporal change of the blood flow velocity appearing in pulsing and rheology of blood and blood rheology is calculated from the change of the blood flow velocity appearing in pulsing. For example, when the change of the blood flow is large, it is regarded that there is brought about a state in which the viscosity of blood is low.

Next, an explanation will be given of the blood rheology measuring method of the embodiment. FIG. 1 shows the graph of the temporal change of the blood flow velocity accompanied by pulsing. As a characteristic component of blood rheology, the maximum blood flow velocity Vx is pointed out. As shown by the following equation, the maximum blood flow velocity Vx is corrected to be V1 by using a correction coefficient C1.

$$V1 = C1 \times Vx$$

When the blood rheology measuring method of the invention is applied to a person having blood rheology in which the total blood pass time period calculated by using the maximum blood flow velocity Vx and the micro-channel array is 60 sec to thereby calculate the pulse velocity waveform and the correction coefficient C1 is calculated such that V1 becomes 60, in the case in which the total blood pass time period of the same person is changed to 35 sec, when V1 is calculated from Equation 1 by using C1 calculated above, V1 shows a value of 35.

Further, the ratio Vn of the maximum blood flow velocity. Vx as compared with the pulse velocity waveform, is correlated with blood rheology and Vn is calculated by dividing the maximum blood flow velocity Vx by the integrated value of the pulse velocity waveform. That is, Vn is calculated by following Equation 1. As mentioned above, Equation 1 is expressed as Vn=CxVx/(integrated value of pulse velocity waveform).

Incidentally, in the case in which the blood rheology measuring method of the embodiment is applied to a person having blood rheology in which the total blood pass time period calculated by using the micro-channel array according to the conventional method is 60 sec to thereby calculate the pulse velocity waveform and the correction coefficient C is calculated such that Vn of Equation 1 becomes 60, when the total pass time period of the same person is changed to 35 sec, when Vn is calculated from Equation 1 by using C calculated above, there is shown a value of 35 with an error of ±8%. Either of V1 and Vn can be found to be correlated with blood rheology and therefore, the analysis may be carried out by either of the methods.

Embodiment 2

Figure 9:
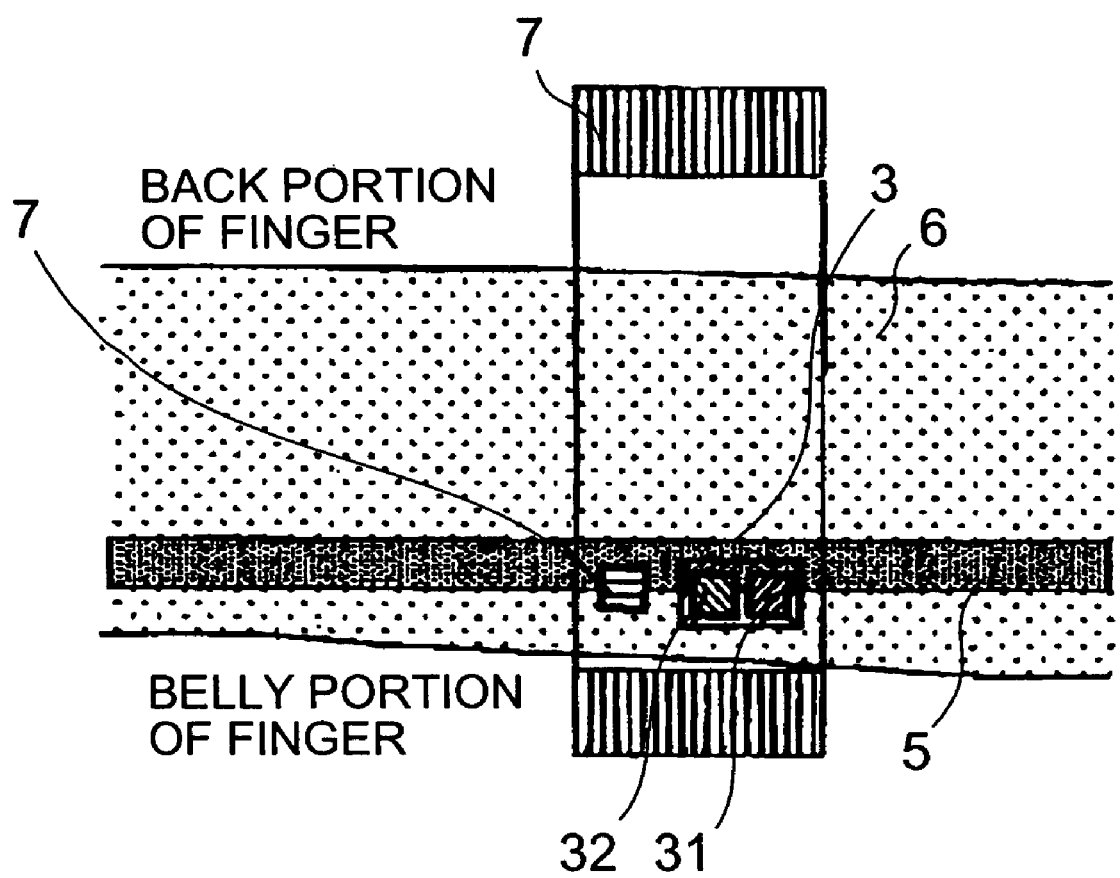
FIG. 9 is an explanatory view of Embodiment 2 according to the invention and is a perspective sectional view of inside of a finger ring viewing from the B direction shown in FIG. 6B.

According to Embodiment 2 of the invention, there is provided body temperature compensating means to above Embodiment 1. A mode of putting the blood rheology measuring apparatus on the finger is similar to that of FIG. 6. Further, FIG. 9 shows a perspective sectional view of the finger ring portion 1 viewing from the B direction of FIG. 6B. The blood rheology measuring apparatus of Embodiment 2 is constituted by being classified in two of the finger ring portion 1 and the signal processing portion 2 similar to Embodiment 1 and as shown by FIG. 9, there are present the ultrasonic wave sensor portion 3 and a temperature sensor 7 on the inner side of the finger ring portion 1. Further, also the temperature sensor 7 is attached to the portion of the finger 6 shifted to the left of the center of the belly in order to measure temperature at a vicinity of the artery 5 similar to the ultrasonic sensor portion. Thereby, reflection from the artery can firmly be caught and accuracy of measuring blood flow is promoted. Although according to Embodiment 2, the portions are attached to shift to the left, even when the portions are attached to shift to the right to aim at the artery on the right side, the effect stays the same.

The blood rheology measuring apparatus of Embodiment 2 is normally portable by mounting the finger ring portion 1 to the finger 6 and mounting the signal processing portion 2 to the arm. Further, also the signal processing portion 2 may be mounted to the finger 6 similar to the finger ring portion 1. The signal processing portion 2 and the ultrasonic wave incident portion 31, the ultrasonic wave detecting portion 32 and the temperature sensor portion 7, are connected by lead wires. The driving voltage signal is inputted from the signal processing portion 2 to the ultrasonic wave incident portion 31 via the lead wire and at the ultrasonic wave detecting portion 32, the measured voltage signal is inputted to the signal processing portion 2. Further, a temperature signal of the temperature sensor 7 is outputted to the signal processing portion 2 via the lead wire.

Figure 10:
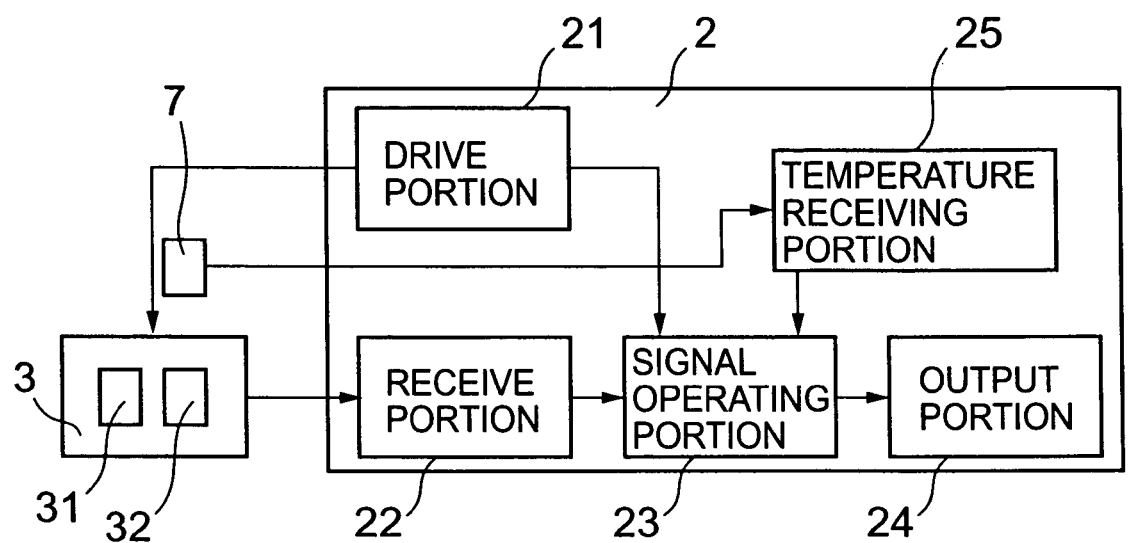
FIG. 10 is a block diagram showing an inner constitution of a signal processing portion of a blood rheology measuring apparatus of Embodiment 2 (Embodiments 4, 5, 6) and a state of connecting the signal processing portion, an ultrasonic sensor portion at inside of a finger ring portion and a temperature sensor.

FIG. 10 shows a block diagram showing an inner constitution of the signal processing portion 2 of the blood rheology measuring apparatus of Embodiment 2 and a state of connecting the signal processing portion 2, the ultrasonic wave sensor portion 3 and the temperature sensor 7 at inside of the finger ring portion 1. As illustrated, the signal processing portion 2 is generally constituted by the drive portion 21, the receive portion 22, the signal operating portion 23, the output portion 24 and a temperature receiving portion 25. A difference between Embodiment 1 and Embodiment 2 resides in that the temperature sensor 7 and the temperature receiving portion 25 are further installed and temperature compensating operation is carried out in the operational processing at the signal operating portion 23 and according to the embodiment, when the blood flow velocity is calculated, the blood flow velocity is corrected by using temperature at a vicinity of the artery 5 of the finger portion 6 received by the temperature receiving portion 25. The artery 5 of the finger portion 6 is sensitive to a change in temperature, the artery is contracted at low temperature, the blood flow velocity is reduced and therefore, by compensating for an amount of a change in the blood flow caused by expansion or contraction of the blood vessel based on body temperature information by the temperature sensor, information in correspondence with blood flow rheology can accurately be provided.

When temperature is measured in calculating blood flow velocity and calculating to correct the blood flow velocity by the temperature to thereby determine the correction coefficient C by using a pulse velocity waveform calculated thereby as shown in Embodiment 2, in the calculation for calculating Vn, blood rheology can be calculated with an error of ±5%. Promotion of accuracy of 3% can be confirmed in comparison with the error of ±8% in Embodiment 1 in which temperature compensation is not carried out. Further, generally, the blood vessel is contracted in a state of low temperature and flow of blood to a distal end is extremely deteriorated. When the blood vessel is conversely warmed, a constant circulating state is constituted. It seems that influence of the temperature is difficult to be effected when the blood vessel is warmed up to about the body temperature (36° C.). Therefore, when the blood vessel at a periphery of a measured portion is expanded by providing a heat generating body at a vicinity of the measured portion, the change in blood flow can accurately be measured with excellent reproducibility and accordingly, information with regard to blood rheology can accurately be assessed.

As a heat generating body, a heater or the like can also be used and when a piezoelectric element of PZT or the like is used for transmitting an ultrasonic wave as a measuring portion, the piezoelectric element per se generates heat and therefore, the piezoelectric element can also be utilized.

Further, in order to accurately measure temperature, or effectively transmit heat of a heat generating body, it is preferable that the finger ring portion 1 is made of a material which is difficult to transmit heat and ceramics or the like is pertinent therefor. Further, generally, when the pulse number is increased, the blood flow velocity is also increased and therefore, when the pulse number is increased to be larger than that at normal occasion, by measuring the pulse number and carrying out a correction by the pulse number (for example, dividing the blood flow velocity by the pulse number or the like), the measurement accuracy can further be promoted. The pulse number can be measured by measuring a temporal interval of peaks of the blood flow velocity in FIG. 1 for respective pulse and constituting a number inverse thereto.

Embodiment 3

Figure 11:
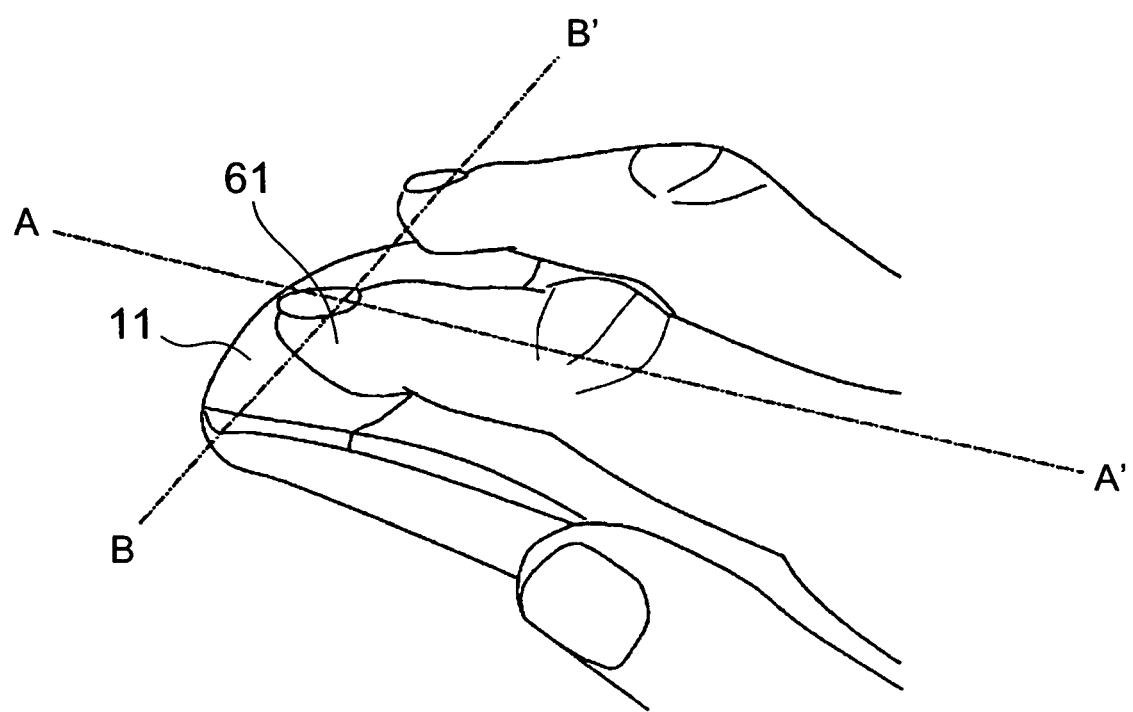
FIG. 11 is a view showing an outlook constitution of a blood rheology measuring apparatus constituting Embodiment 3 (Embodiment 4)

FIG. 11 is a view showing an outlook constitution of a blood rheology measuring apparatus according to a third embodiment of the invention. Although the embodiment is similar to above Embodiment 1 in that the embodiment is constituted by the first blood rheology analyzing method according to the invention of calculating blood rheology by dividing the maximum blood flow velocity Vx shown in FIG. 1 by the integrated value of the pulse velocity waveform (the integrated value of the pulse velocity waveform in one period of pulse), the embodiment differs from Embodiment 1 in that a position of measuring blood flow is basically disposed at a finger tip portion frontward from the first joint of the finger. As shown by FIG. 11, the blood rheology measuring apparatus is constructed by a constitution including the signal processing portion 2 in a mouse-type blood rheology measuring apparatus 11.

Figure 12:
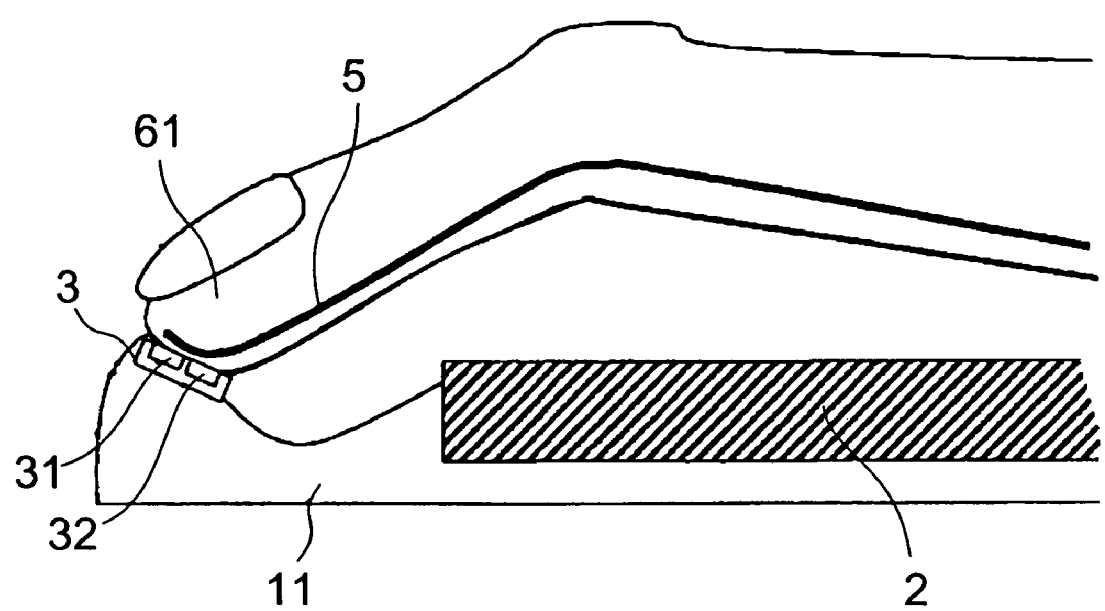
FIG. 12 illustrates a section taken along a line A-A' of FIG. 11 with respect to Embodiment 3.

FIG. 12 illustrates a section taken along a line A-A' of FIG. 11. As shown by FIG. 12, the ultrasonic wave sensor portion 3 is present on an upper side of the mouse type blood rheology measuring apparatus 11. The ultrasonic wave sensor portion 3 is attached with the ultrasonic wave incident portion 31 and the ultrasonic wave detecting portion 32 to be brought into contact with the belly portion of the finger tip 61. Further, the artery 5 present in the finger tip 61 passes the belly portion of the finger tip 61 and therefore, in order to measure flow of blood of the artery 5, the ultrasonic wave incident portion 31 and the ultrasonic wave detecting portion 32 are attached to the central portion of the belly of the finger tip 61 as shown by FIG. 12 such that an ultrasonic wave can be made accurately incident to aim at the artery 5 (including the capillary artery).

Figure 13:
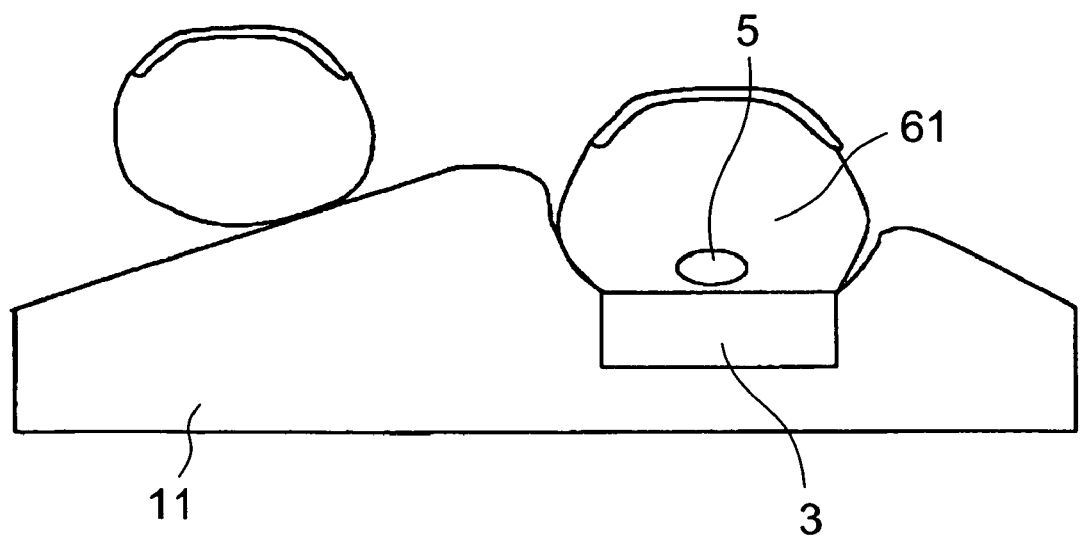
FIG. 13 illustrates a section taken along a line B-B' of FIG. 11 with respect to Embodiment 3.

Further, FIG. 13 illustrates a section taken along a line B-B' of FIG. 11. As shown by FIG. 13, the apparatus is recessed such that the central portion of the belly of the finger tip 61 is disposed at the ultrasonic wave sensor portion 3. Thereby, reflection from the artery 5 can firmly be caught and accuracy of measuring blood flow is promoted. Although according to Embodiment 3, the mode of the apparatus is constituted by the mouse type, the mode is not limited thereto but the blood rheology measuring apparatus can be constituted by installing the sensor at the position brought into contact with the finger tip as in Embodiment 3 so far as the apparatus can be gripped by the finger.

The blood rheology measuring apparatus of Embodiment 3 is portable since the signal processing portion 2 is included in the mouse type blood rheology measuring apparatus 11. The signal processing portion 2 and the ultrasonic wave incident portion 31 and the ultrasonic detecting portion 32 installed at the mouse type blood rheology measuring apparatus 11 are connected by lead wires, the driving voltage signal is inputted from the signal processing portion 2 to the ultrasonic incident portion 31 via the lead wire and at the ultrasonic wave detecting portion 32, the measured voltage signal is inputted to the signal processing portion 2.

A block diagram showing the inner constitution of the signal processing portion 2 of the blood rheology measuring apparatus of Embodiment 3 and the state of connecting the signal processing portion 2 and the ultrasonic wave sensor portion 3 at inside of the mouse type blood rheology measuring apparatus 11, is basically the same as FIG. 8 of Embodiment 1. As illustrated, the signal processing portion 2 is generally constituted by the drive portions 21, the receive portion 22, the signal operating portion 23 and the output portion 24. The drive portion 21 of Embodiment 3 oscillates PZT installed at the ultrasonic wave incident portion 31 and transmits drive voltage for making an ultrasonic wave incident on the artery 5. The receive portion 22 receives voltage generated when PZT installed at the ultrasonic wave detecting portion 32 receives the ultrasonic wave. The signal operating portion 23 carries out various processings with regard to measurement of blood rheology by executing processing programs stored to a storage region (illustration is omitted) provided at inside thereof and outputs a result of the processings to the output portion 24.

Further, the signal operating portion 23 calculates the Doppler effect of blood flow by comparing the frequency of the ultrasonic wave emitted from the ultrasonic wave incident portion 31 and the frequency of the ultrasonic wave received by the ultrasonic wave detecting portion 32. Further, the signal operating portion 23 calculates the velocity of blood flow flowing in the artery 5 by a change in the frequency and calculates the temporal change of the velocity. Further, the form of the temporal change of the blood flow velocity appearing in pulsing, is correlated with rheology of blood and blood rheology is calculated from a change in the blood flow velocity appearing in pulsing.

Also according to the blood rheology measuring method of the embodiment, blood rheology is calculated by following Equation 1. The ratio Vn of the maximum blood flow velocity Vx as compared with the pulse velocity waveform, is correlated with blood rheology and Vn is calculated by dividing the maximum blood flow velocity Vx by the integrated value of the pulse velocity waveform. As described above, Equation 1 is expressed as Vn=CxVx/(integrated value of pulse velocity waveform). Incidentally, when the correction coefficient C is calculated such that Vn of Equation 1 becomes 60 by calculating the pulse velocity waveform by applying the blood rheology measuring method of the embodiment to a person having blood rheology in which the total pass time period calculated by using the micro-channel array of the conventional method, is 60 sec, in the case in which the total blood pass time period of the same person is changed to 35 sec, when Vn is calculated from Equation 1 by using C calculated above, a value of 35 is shown with an error of ±8%.

Further, a constant correlation is confirmed even with V1=CxVx and therefore, the analysis can be carried out by either of the methods.

Embodiment 4

Figure 14:
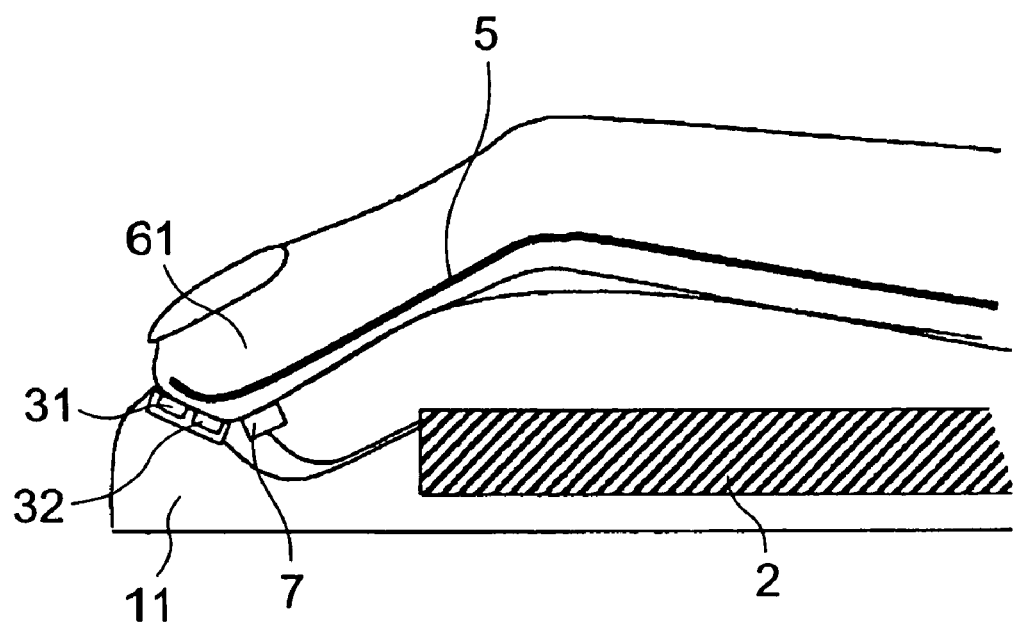
FIG. 14 is a view showing a sectional view of a mouse type blood rheology measuring apparatus of Embodiment 4, illustrating a section taken along a line A-A' of FIG. 11.

FIG. 14 is a view showing a sectional view of the mouse type blood rheology measuring apparatus 11 according to a fourth embodiment of the invention. Although the blood rheology measuring apparatus of Embodiment 4 is constructed by a constitution including the signal processing portion 2 in the mouse type blood rheology measuring apparatus 11 similar to Embodiment 3, as shown by FIG. 14, the ultrasonic sensor portion 3 and the temperature sensor 7 are installed on the inner side of the mouse type blood rheology measuring apparatus 11 to thereby provide body temperature compensating means. Further, similar to Embodiment 3, the ultrasonic wave sensor portion 3 is attached with the ultrasonic wave incident portion 31 and the ultrasonic wave detecting portion 32 to be brought into contact with the belly portion of the finger tip 61. Further, the artery 5 disposed in the finger tip 61 passes the belly portion of the finger tip 61 and therefore, in order to measure flow of blood of the artery, the ultrasonic wave incident portion 31 and the ultrasonic wave detecting portion 32 are attached to the central portion of the belly of the finger tip 61 as shown by FIG. 14 such that an ultrasonic wave can be incident accurately to aim at the artery 5. Further, also the temperature sensor 7 is attached to the central portion of the belly of the finger tip 61 similar to the ultrasonic wave sensor portion 3 in order to measure temperature at a vicinity of the artery 5. Thereby, reflection of the artery 5 can firmly be caught and accuracy of measuring blood flow is promoted.

The temperature sensor portion 7 is connected to the signal processing portion 2 by the lead wire similar to the ultrasonic wave incident portion 31 and the ultrasonic wave detecting portion 32 installed at the mouse type blood rheology measuring apparatus 11. The temperature signal of the temperature sensor 7 is outputted to the signal processing portion 2 via the lead wire.

A block diagram showing the inner constitution of the signal processing portion 2 of the blood rheology measuring apparatus of Embodiment 4 and the state of connecting the signal processing portion 2 and the ultrasonic sensor portion 3 at inside of the mouse type blood rheology measuring apparatus 11, is basically the same as FIG. 10 of Embodiment 2. As illustrated, the signal processing portion 2 is generally constituted by the drive portion 21, the receive portion 22, the signal operating portion 23 and the output portion 24. A difference between Embodiment 3 and Embodiment 4 resides in that the temperature sensor 7 and the temperature receiving portion 25 are further installed and the temperature compensating operation is carried out by the operational processing at the signal operating portion 23 and according to the embodiment, in calculating the blood flow velocity, the blood flow velocity is corrected by using the temperature at a vicinity of the artery 5 of the finger portion 6 received by the temperature receiving portion 25. The artery 5 of the finger portion 6 is sensitive to a change in temperature, when temperature becomes low, the artery is contracted, the blood flow velocity is reduced and therefore, by compensating for an amount of the change in the blood flow caused by expansion or contraction of the blood vessel based on the body temperature information by the temperature sensor, information in correspondence with blood rheology can accurately be provided similar to Embodiment 2.

In calculating the blood flow velocity by Embodiment 4, when the temperature is measured and the blood flow velocity is calculated by correcting the blood flow velocity by the temperature to thereby determine the correction coefficient C by using the pulse velocity waveform calculated thereby, in the calculation of calculating Vn, blood rheology can be calculated with an error of ±4%. Promotion of accuracy of 4% can be confirmed in comparison with the error of ±8% in Embodiment 3 in which temperature compensation is not carried out.

Embodiment 5

Figure 15:
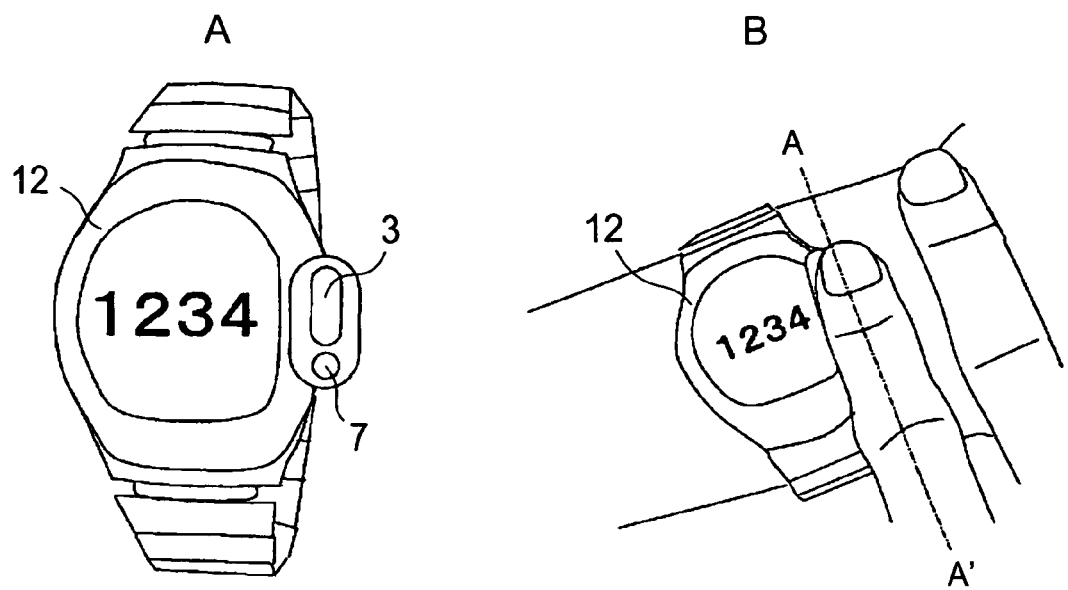
Figure 16:
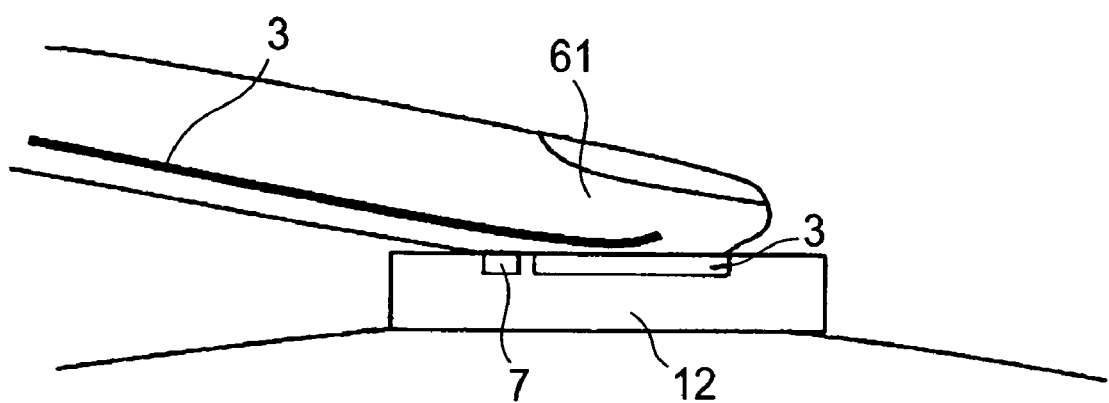
FIG. 16 illustrates a section taken along a line A-A' of FIG. 15B of the wrist watch type blood rheology measuring apparatus constituting the fifth embodiment.

FIG. 15A is an outlook view of a wrist watch type blood rheology measuring apparatus 12 according to a fifth embodiment of the invention and FIG. 15B is a view showing a measuring state of the wrist watch type blood rheology measuring apparatus 12. FIG. 16 illustrates a section taken along a line A-A' of FIG. 15B.

The blood rheology measuring apparatus of Embodiment 5 is constructed by a constitution including the signal processing portion 2 (not illustrated) in the wrist watch type blood rheology measuring apparatus 12. Further, as shown by FIG. 16, there are present the ultrasonic wave sensor portion 3 and the temperature sensor 7 on an inner side of a wrist watch. Further, similar to Embodiment 4, the ultrasonic wave sensor portion 3 is attached with the ultrasonic wave incident portion 31 and the ultrasonic wave detecting portion 32 to be brought into contact with the portion of the belly of the finger tip 61. Further, the artery 5 disposed in the finger tip 61 passes the belly portion of the finger tip 5 and therefore, in order to measure flow of blood of the artery 5, the ultrasonic wave incident portion 31 and the ultrasonic wave detecting portion 32 are attached to be brought into contact with the central portion of the belly of the finger tip 61 such that an ultrasonic wave can accurately be incident to aim at the artery 5. Further, also the temperature sensor 7 is attached to the central portion of the belly of the finger tip 61 similar to the ultrasonic sensor portion 3 to measure temperature at a vicinity of the artery 5. Thereby, reflection from the artery 5 can firmly be caught and accuracy of measuring blood flow is promoted.

As shown by FIG. 16, the temperature sensor 7 is disposed not on the side of the finger tip of the ultrasonic sensor portion 3 but on the palm side. The reason is that when the temperature sensor 7 is installed on the side of the finger tip of the ultrasonic wave sensor portion 3, the temperature sensor 3 is not brought into contact with the finger tip and accurate temperature cannot be measured.

The blood rheology measuring apparatus of Embodiment 5 is normally portable since the signal processing portion 2 is included in the wrist watch type blood rheology measuring apparatus 12. The signal processing portion 2, and the ultrasonic wave incident portion 31, the ultrasonic wave detecting portion 32 and the temperature sensor portion 7 installed in the wrist watch type blood rheology measuring apparatus 12, are connected by lead wires. The driving voltage signal is inputted from the signal processing portion 2 to the ultrasonic wave incident portion 31 via the lead wire and at the ultrasonic wave detecting portion 32, the measured voltage signal is inputted to the signal processing portion 2. Further, the temperature signal of the temperature sensor 7 is outputted to the signal processing portion 2 via the lead wire. The output can be outputted to a display screen of the wrist watch.

A block diagram showing the inner constitution of the signal processing portion of the wrist watch type blood rheology measuring apparatus 12 of Embodiment 5 and the state of connecting the signal processing portion 2, the ultrasonic wave sensor portion 3 and the temperature sensor 7 at inside of the wrist watch type blood rheology measuring apparatus 12, is basically the same as FIG. 10. As illustrated, the signal processing portion 2 is generally constituted by the drive portion 21, the receive portion 22, the signal operating portion 23, the output portion 24 and the temperature receiving portion 25.

The blood rheology measuring method of the embodiment is calculated by following Equation 1 and the temperature compensation is carried out based on the body temperature detected value similar to Embodiment 2 and Embodiment 4.

Embodiment 6

Figure 17:
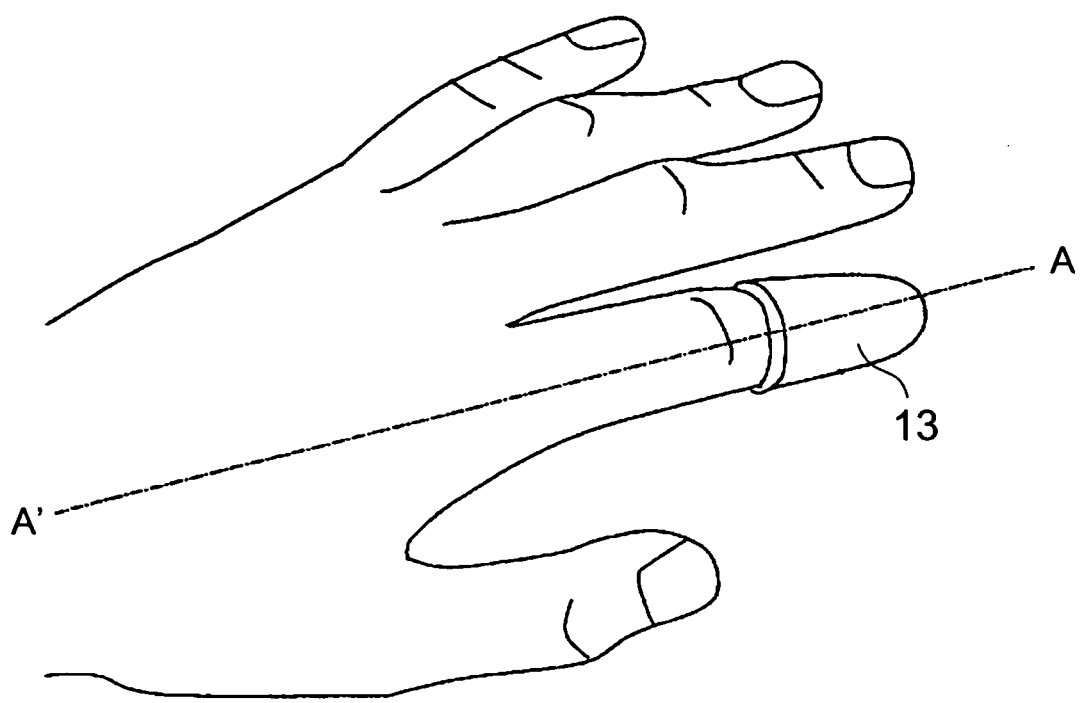
FIG. 17 is a constitution view of an outlook of a finger sack type blood rheology measuring apparatus of a blood rheology measuring apparatus constituting a sixth embodiment of the invention.
Figure 18:
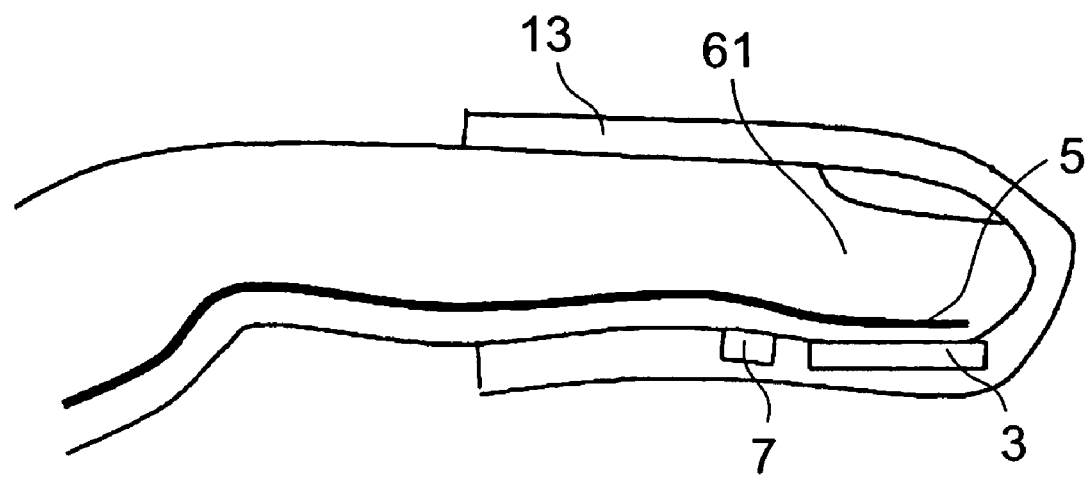
FIG. 18 illustrates a section taken along a line A-A' of FIG. 17 according to the sixth embodiment of the invention.

FIG. 17 illustrates a constitution view of an outlook of a finger sack type blood rheology measuring apparatus 13 of a blood rheology measuring apparatus according to a sixth embodiment of the invention and FIG. 18 illustrates a section taken along a line A-A' of FIG. 17. The blood rheology measuring apparatus of Embodiment 6 is constituted by being classified into the finger sack type blood rheology measuring apparatus 13 and the signal processing portion 2. As shown in FIG. 18, there are present the ultrasonic wave sensor portion 3 and the temperature sensor 7 on an inner side of the finger sack type blood rheology measuring apparatus 13.

Similar to Embodiment 4, the ultrasonic wave sensor portion 3 is attached with the ultrasonic wave incident portion 31 and the ultrasonic wave detecting portion 32 to be brought into contact with the portion of the belly of the finger tip 61. Further, the artery 5 disposed in the finger tip 61 passes the belly portion of the finger tip 61 and therefore, in order to measure flow of blood of the artery, the ultrasonic wave incident portion 31 and the ultrasonic wave detecting portion 32 are attached to be brought into contact with the central portion of the belly of the finger tip 61 such that an ultrasonic wave can accurately be incident to aim at the artery 5.

Further, also the temperature sensor 7 is attached to the central portion of the belly of the finger tip 61 similar to the ultrasonic wave sensor portion 3 in order to measure temperature at a vicinity of the artery. Thereby, reflection from the artery 5 can firmly be caught and accuracy of measuring blood flow is promoted.

The blood rheology measuring apparatus of Embodiment 6 can normally be carried and can carry out measurement normally by mounting the finger sack type blood rheology measuring apparatus 13 to the finger tip and carrying the signal processing portion 2 (not illustrated) on the arm. Further, the signal processing portion 2 can also be included in the finger sack type blood rheology measuring apparatus 13.

The signal processing portion 2 and the ultrasonic wave incident portion 31, the ultrasonic wave detecting portion 32 and the temperature sensor portion 7 installed at the finger sack type blood rheology measuring apparatus 13, are connected by lead wires. The driving voltage signal is inputted from the signal processing portion 2 to the ultrasonic wave incident portion 31 via the lead wire and at the ultrasonic wave detecting portion 32, the measured voltage signal is inputted to the signal processing portion 2. Further, the temperature signal of the temperature sensor 7 is outputted to the signal processing portion 2 via the lead wire.

A block diagram showing the inner constitution of the signal processing portion 2 of the finger sack type blood rheology measuring apparatus 13 of Embodiment 6 and the state of connecting the signal processing portion 2, the ultrasonic wave sensor portion 3 and the temperature sensor 7 at inside of the wrist watch type blood rheology measuring apparatus 12, is basically similar to FIG. 10.

The blood rheology measuring method of the embodiment is calculated by following Equation 1 and the temperature compensation is carried out based on the body temperature detected value similar to Embodiment 2, Embodiment 4 and Embodiment 5.

Further, also according to the finger sack type blood rheology measuring apparatus explained in the embodiment, by providing a cuff structure, mentioned later, as in FIG. 25, a change in blood flow velocity by a change in blood pressure and accordingly, a change in blood rheology can be corrected.

Embodiment 7

An explanation will be given of Embodiment 7 through Embodiment 10 as follows and with regard to these embodiments, measurement data of five subjects is sampled and an investigation is carried out on a comparison thereof. Before explaining the respective embodiments, there is shown basic data of measuring highest blood pressure, lowest blood pressure and a measured total blood pass time period value before meal and after meal with respect to the five subjects in Table 1.

TABLE 1

| Subject | Condition | Highest blood pressure | Lowest blood pressure | micro-channel (sec) |
|---|---|---|---|---|
| A | before meal | 115.0 | 63.5 | 56.3 |
|   | after meal | 110.5 | 63.5 | 52.7 |
| B | before meal | 109.0 | 75.0 | 43.1 |
|   | after meal | 100.0 | 62.5 | 41.2 |
| C | before meal | 119.0 | 89.0 | 48.7 |
|   | after meal | 106.5 | 79.0 | 44.1 |
| D | before meal | 194.0 | 133.0 | 54.1 |
|   | after meal | 175.0 | 122.0 | 52.3 |
| E | before meal | 109.5 | 77.0 | 52.5 |
|   | after meal | 110.0 | 71.5 | 44.0 |

Next, an explanation will be given of a blood rheology measuring apparatus according to a seventh embodiment of the invention. According to the embodiment, there is used a finger ring type sensor as shown by FIG. 6 and FIG. 7 as a blood flow velocity detecting portion and there is adopted the second method, that is, a method of sampling a maximum frequency from a frequency waveform as a method of analyzing blood rheology. By using Embodiment 7, the five subjects are measured and there are provided a maximum frequency indicating blood rheology and a value produced by dividing the maximum frequency by a highest blood pressure value. The data is shown in Table 2.

TABLE 2

| Subject | Condition | Maximum frequency | Maximum frequency/Highest blood pressure |
|---|---|---|---|
| A | before meal | 914 | 7.9 |
|   | after meal | 703 | 6.4 |
| B | before meal | 1669 | 15.3 |
|   | after meal | 1918 | 19.2 |
| C | before meal | 1014 | 8.5 |
|   | after meal | 1688 | 15.9 |
| D | before meal | 1100 | 5.7 |
|   | after meal | 1856 | 10.6 |
| E | before meal | 1177 | 10.7 |
|   | after meal | 1315 | 12.0 |

Figure 19:
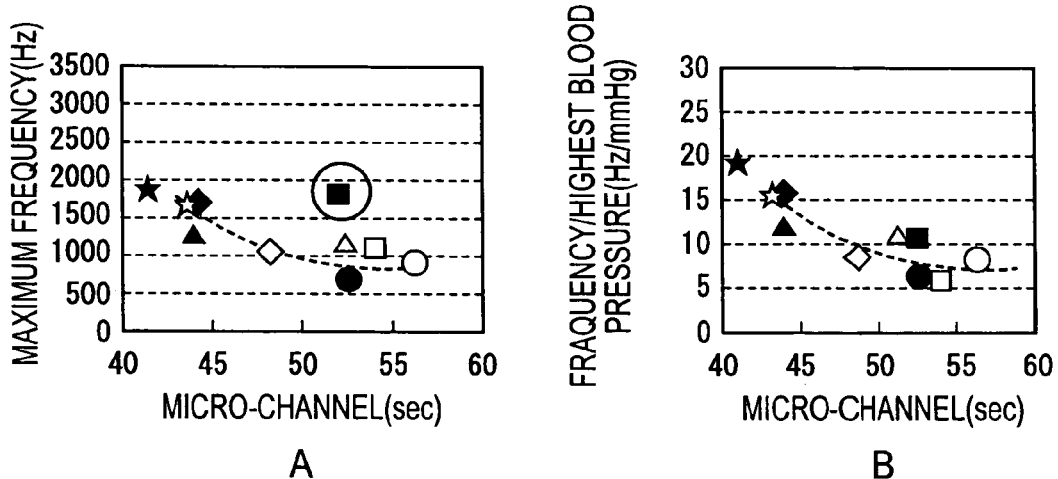
FIGS. 19A and 19B indicate data of a seventh embodiment of the invention by graphs.

FIGS. 19A and 19B show the data indicated by graphs in which FIG. 19A shows a correspondence between the maximum frequency and the micro-channel and FIG. 19B shows a correspondence between the value produced by dividing the maximum frequency by the highest blood pressure value and the micro-channel. When a result thereof is observed, it is known from the graph of FIG. 19A that a correlation is established without taking an individual difference into consideration except data of subject D having a high blood pressure value in the data adopting data of the second method of analyzing blood rheology based on the artery blood flow information at the finger position (by providing a frequency histogram from Doppler shift intensity information, further providing a frequency waveform and providing a maximum frequency thereof). The correlation can be grasped not as a linear relationship but as a relationship of a quadratic curve as indicated by a broken line. There is an enormous significance in that although in the case of data of the first method of analyzing blood rheology, it is necessary to sample blood and calculate the correction value C of an individual by measurement by the micro-channel array, according to the embodiment, the data can directly be measured. Further, it is known from the graph of FIG. 19B that there is established a correlation with regard to data produced by dividing data of the second method of analyzing blood rheology based on the artery blood flow information at the finger position by a blood pressure value without taking an individual difference into consideration including data of subject D having a high blood pressure value. The correlation can be grasped not as a linear relationship but as a relationship of a quadratic curve as shown by a broken line. It is found that the embodiment excellently corrects an amount of variation by blood pressure and can be regarded as a compensation method particularly effective for subjects having high blood pressure and low blood pressure.

Embodiment 8

In the case of a blood rheology measuring apparatus according to an eighth embodiment of the invention, there is detected blood flow velocity of the artery of the finger tip by using a mouse type sensor as shown by FIG. 11 through FIG. 13 as a blood flow velocity detecting portion and as a method of analyzing blood rheology, the second method, that is, a method of sampling the maximum frequency from the frequency waveform is adopted. By using Embodiment 8, five subjects are measured and there are provided the maximum frequency indicating blood rheology and the value produced by dividing the maximum frequency by the highest blood pressure value. The data is shown in Table 3.

TABLE 3

| Subject | Condition | Maximum frequency | Maximum frequency/ Highest blood pressure |
| --- | --- | --- | --- |
| A | before meal | 904 | 7.9 |
|   | after meal | 1315 | 11.9 |
| B | before meal | 2024 | 18.6 |
|   | after meal | 2557 | 25.6 |
| C | before meal | 1846 | 15.5 |
|   | after meal | 2062 | 19.4 |
| D | before meal | 2880 | 14.8 |
|   | after meal | 2139 | 12.2 |
| E | before meal | 2047 | 18.7 |
|   | after meal | 1764 | 16.0 |

Figure 20:
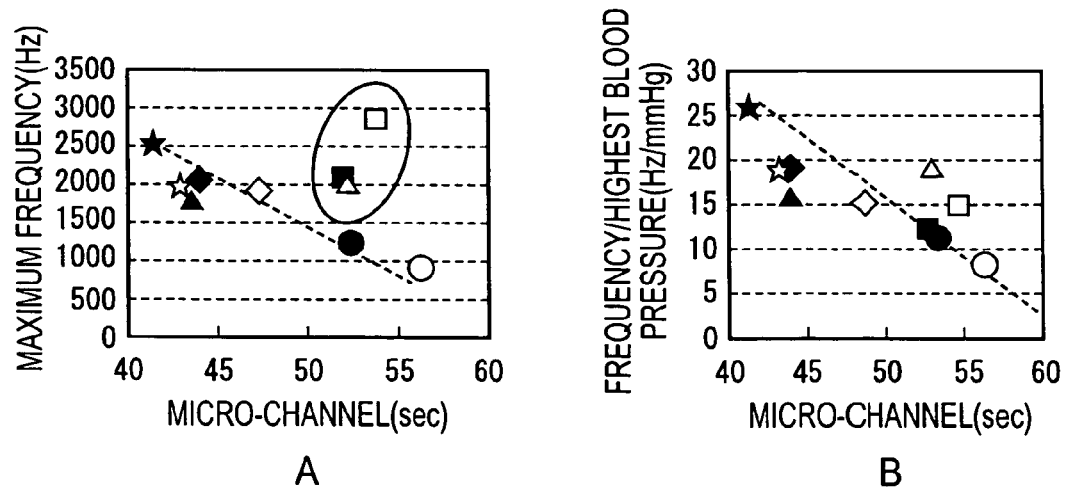
FIGS. 20A and 20B indicate data of an eighth embodiment of the invention by graphs.

FIGS. 20A and 20B indicate the data by graphs in which FIG. 20A shows a correspondence between the maximum frequency and the micro-channel and FIG. 20B shows a correspondence between the value of the maximum frequency divided by the highest blood pressure value and the micro-channel. When a result there of is observed, it is known from the graph of FIG. 20A that a correlation is established without taking an individual difference into consideration except data of subject D having a high blood pressure value in the data adopting data by the second method of analyzing the rheology based on the artery blood flow information at the finger tip position. The correlation can be grasped as a linear relationship according to the embodiment. According to the embodiment, the relationship can directly be measured with no need of calculating the correction value C similar to Embodiment 7. Further, it is known from the graph of FIG. 20B that a correlation is established without taking an individual difference into consideration including data of subject D having a high blood pressure value in the data adopting data of the second method of analyzing blood rheology based on the artery blood flow information at the finger tip position. The correlation can be grasped as the linear relationship as shown by a broken line. According to the embodiment, it is found that an amount of variation by blood pressure is well compensated for and also in the embodiment, the processing of dividing the maximum frequency by the blood pressure value is a compensation method effective for subjects having high blood pressure and low blood pressure.

Embodiment 9

In the case of the blood rheology measuring apparatus according to a ninth embodiment of the invention, there is used a finger ring type sensor as shown by FIG. 6 and FIG. 7 as a blood flow velocity detecting portion and there is adopted a third method, that is, a method of sampling an area of one pulse from the frequency waveform as a method of analyzing blood rheology. Five subjects are measured by using Embodiment 9 and there are provided the area of one pulse indicating blood rheology and the value produced by dividing the area by the height blood pressure value. The data is shown in Table 4.

TABLE 4

| Subject | Condition | Area | Area/Highest blood pressure |
| --- | --- | --- | --- |
| A | before meal | 404 | 3.5 |
|   | after meal | 334 | 3 |
| B | before meal | 1101 | 10.1 |
|   | after meal | 1269 | 12.7 |
| C | before meal | 540 | 4.5 |
|   | after meal | 1048 | 9.8 |
| D | before meal | 547 | 2.8 |
|   | after meal | 1104 | 6.3 |
| E | before meal | 676 | 6.2 |
|   | after meal | 925 | 8.4 |

Figure 21:
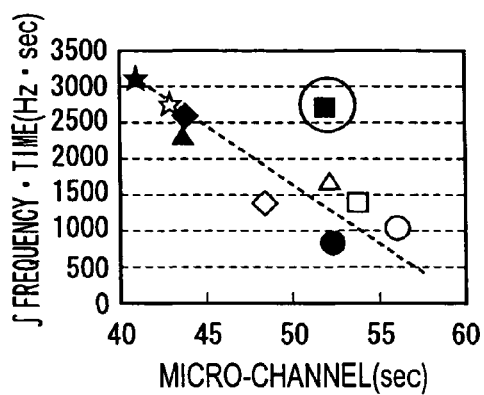
FIGS. 21A and 21B indicate data of a ninth embodiment of the invention by graphs.
Figure 21:
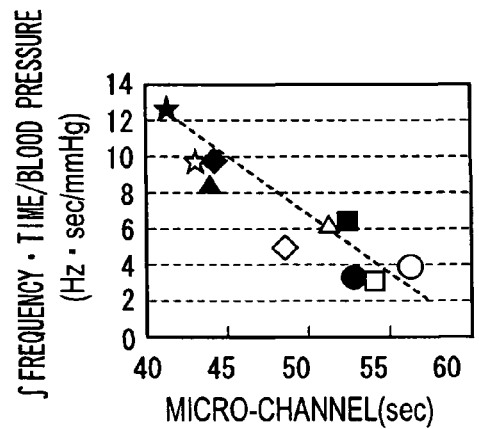

FIGS. 21A and 21B indicate the data by graphs in which FIG. 21A shows a correspondence between the area of one pulse and the micro-channel and FIG. 21B shows a correspondence between a value of the area of one pulse divided by the highest blood pressure and the micro-channel. When a result thereof is observed, it is known from graph A that a correlation is established without taking an individual difference into consideration except data of subject D having a high blood pressure value in the data adopting the data of the third method of analyzing blood rheology based on the artery blood flow information at the finger position (by providing a frequency histogram from Doppler shift intensity information, further providing the frequency waveform and providing the area of one pulse). The correlation can be grasped as a linear relationship as shown by a broken line. According to the embodiment, it is known that the relationship can directly be measured with no need of calculating the correction value C of an individual. Further, it is known from the graph of FIG. 21B that a correlation is established without taking an individual difference into consideration including data of subject D having the high blood pressure value in the data produced by dividing data of the third method of analyzing blood rheology based on the artery blood flow information at the finger position by the blood pressure value. The correlation can be grasped also as a linear relationship. According to the embodiment, it is found that an amount of variation by blood pressure is well compensated for and the embodiment can be regarded as a compensation method particularly effective for subjects having high blood pressure and low blood pressure.

Embodiment 10

Figure 22:
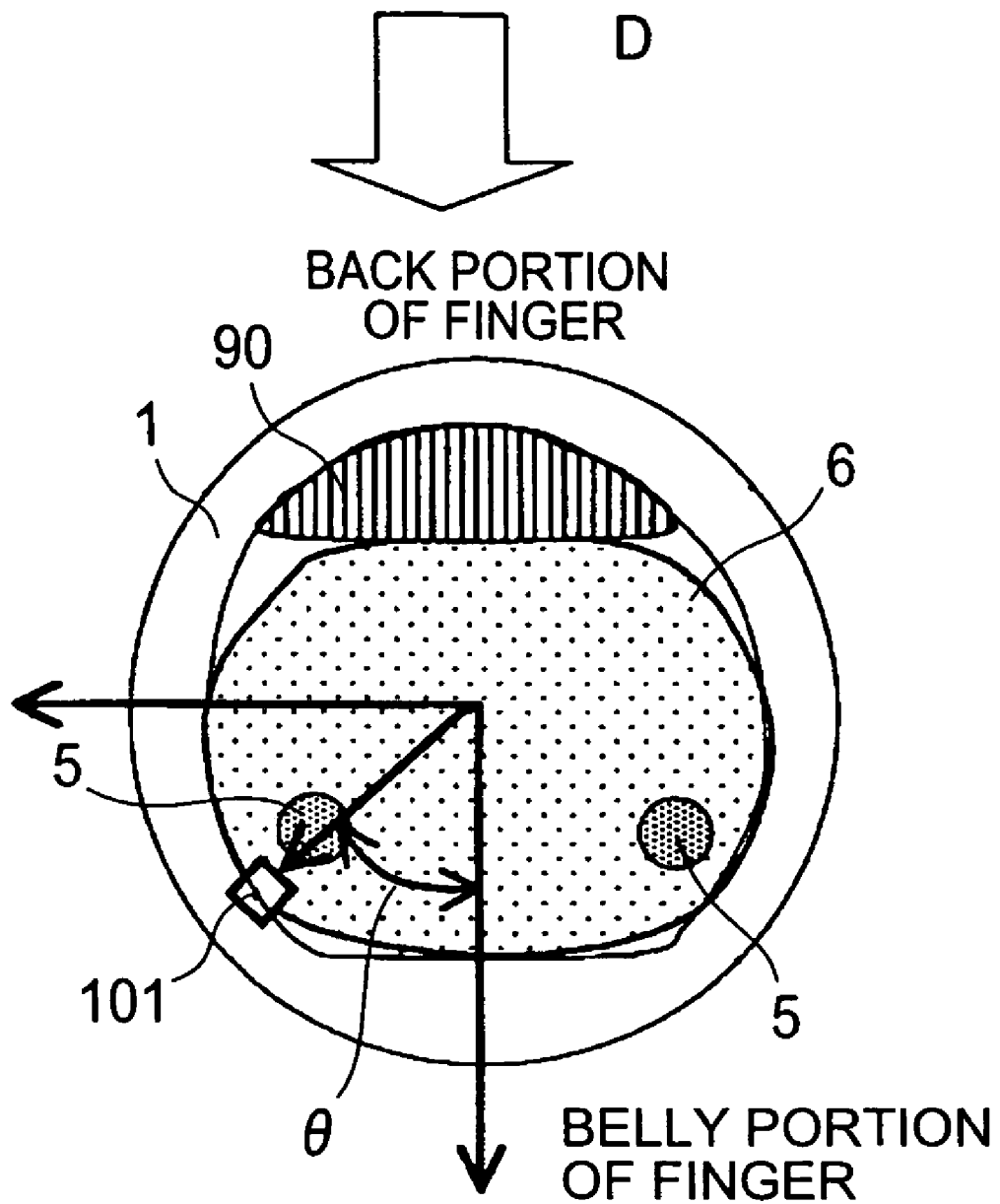
FIG. 22 illustrates a tenth embodiment of the invention.

FIG. 22 is an explanatory view of flattening a portion of the finger ring portion 1 brought into contact with the berry portion of the finger 6 and providing an elastic body 90 of silicone rubber or the like at a gap between the finger 6 and the finger ring portion 1. A position of the artery 5 of the finger tip is disposed at a position at which an angle θ in FIG. 22 falls in a range of about 10 degrees through 80 degrees and when the finger ring portion 1 is constituted by a completely cylindrical shape, positioning of a measuring portion 101 becomes difficult. Therefore, by constituting the shape as shown by FIG. 22, specifying a portion in contact with the belly portion of the finger 6 and arranging a measuring portion 101 with the belly portion as a reference, the measuring portion 101 can precisely be positioned to a vicinity of the artery 5 and reproducibility and reliability of measurement can be promoted.

Further, it is preferable to produce a state in which a space is difficult to produce between the finger 6 and the finger ring portion 1 and the measuring portion 101 and the temperature sensor 7 are brought into close contact with the skin of the finger 6 and do not touch with outside air in using the apparatus.

Therefore, there may be constructed a constitution in which the finger ring portion 1 is fastened by the elastic body 90 of silicone rubber or the like under constant pressure or a seat of silicone rubber or the like is pasted on an inner periphery of the finger ring portion 1 to be brought into close contact with the skin.

Figure 23:
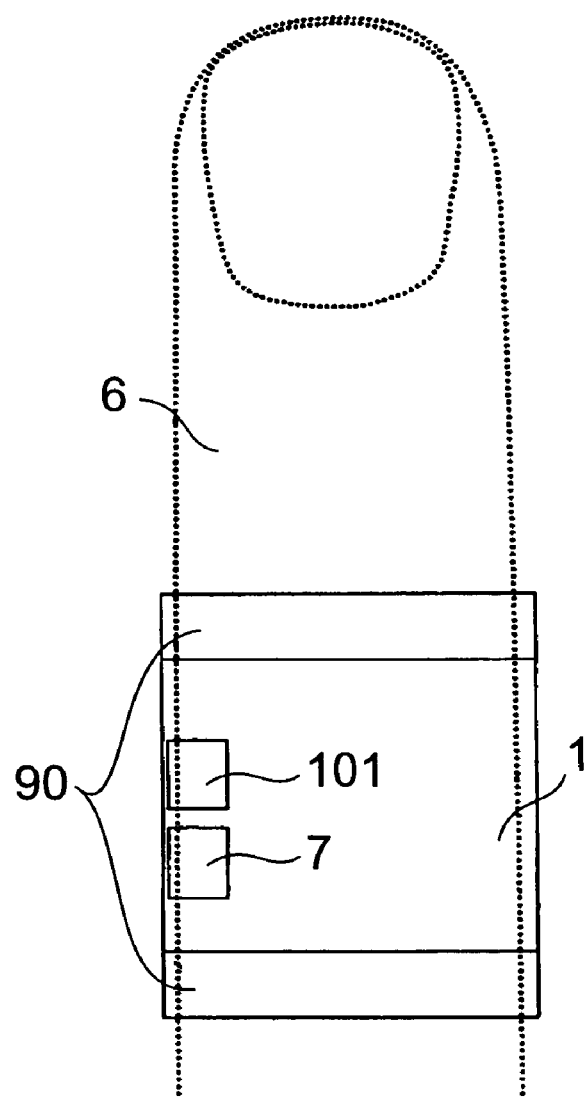
FIG. 23 illustrates the tenth embodiment of the invention.

FIG. 23 is a perspective view viewing the finger ring portion 1 of FIG. 22 from D direction when the elastic body 90 is provided at other position and the temperature sensor 7 is provided. The elastic body 90 is provided to sandwich the measuring portion 101 and the temperature sensor 7, by attaching the finger ring portion 1 to the finger 6, the temperature sensor 7 is prevented from touching the outside air and is made to be difficult to be effected with influence of outside air and accordingly, accuracy of assessing blood rheology can be promoted.

As a material of the elastic body 90, since the elastic body 90 is used by being brought into contact with the living body, in consideration of rash or the like of the skin, silicone rubber having excellent adaptability with the living body is suitable.

Embodiment 11

Figure 24:
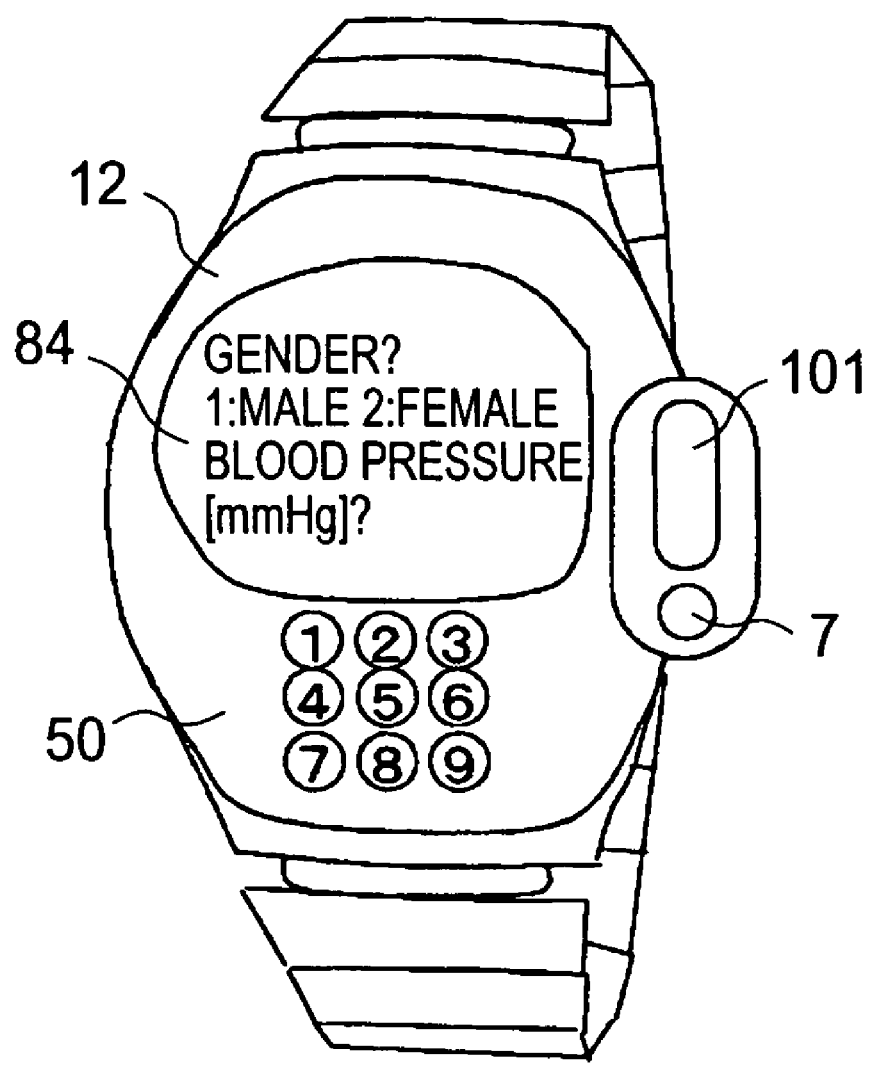
FIG. 24 illustrates an eleventh embodiment of the invention

FIG. 24 is an explanatory view showing a constitution of providing an input portion 50 to the blood rheology measuring apparatus according to Embodiment 4. Generally, the blood flow velocity of the finger tip differs by gender and a blood pressure value, even in the case of the same rheology (total blood pass time period), there is a tendency that a female subject is slower than a male subject and the higher the blood pressure, the faster than blood flow velocity. By correcting the difference by gender and blood pressure, the above-described correlation between the blood flow velocity and blood rheology is improved and reliability of the blood rheology measuring apparatus of the invention is promoted.

By inputting gender and a blood pressure value by the input portion 50, blood rheology can be measured further accurately by using an optimum correction coefficient. Further, eating habit information of a subject (eating when and what, or the like) can be inputted by the input portion 50 and it can be determined whether eating habit and daily life of a subject is suitable for the subject in combination with information with regard to provided blood rheology (for example, by measuring blood rheology before meal and after meal). Further, the input portion may not be of a timepiece type but information can be inputted also by communication from an apparatus having an input portion such as a portable telephone or the like.

Embodiment 12

Figure 25:
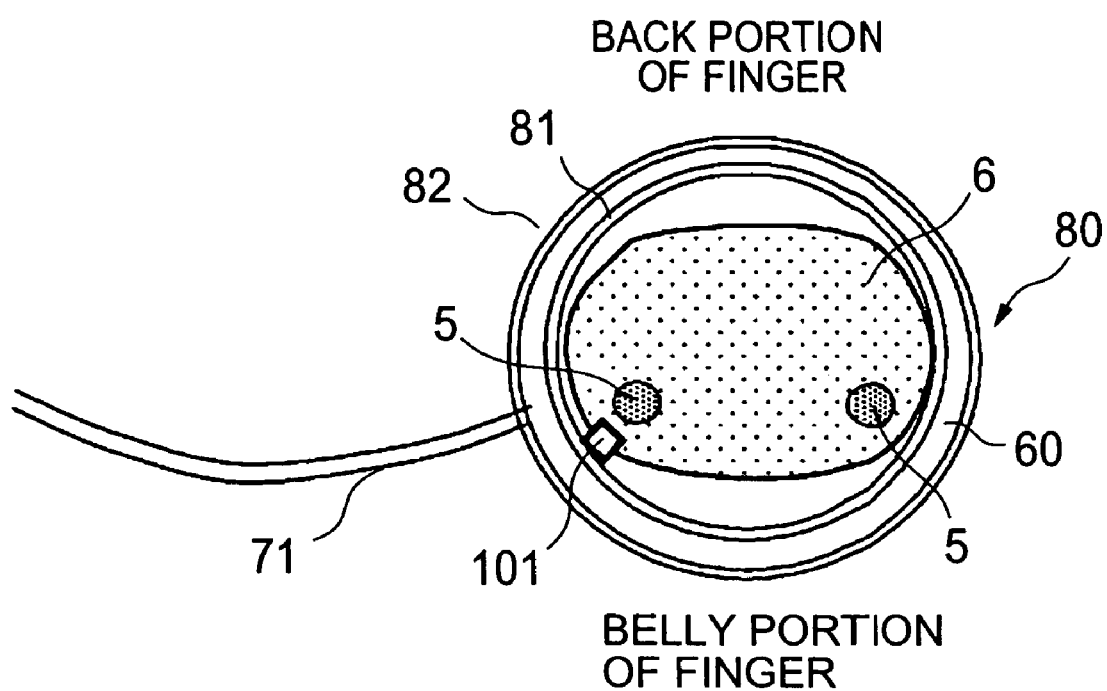
FIG. 25 illustrates a twelfth embodiment of the invention.

FIG. 25 is an explanatory view of a constitution providing the measuring portion 101 at an inner periphery of a cuff 80 mountable to the finger in place of the finger ring portion 1 of the blood rheology measuring apparatus according to Embodiment 2.

The cuff 80 is constituted by a shape of an expand able and contractable bag, comprising an inner periphery 81 and an outer periphery 82 and having an air layer 60. The air layer 60 is connected with a tube 71 and predetermined pressure can be applied from a pressure applying portion, not illustrated, to the air layer 60.

Generally, according to a noninvasive blood pressure meter, the artery is pressurized by a cuff, pressure in starting to flow blood flow (Korotkoff's sound starts to be heard) is defined as the highest blood pressure and pressure in starting to flow constant blood flow (Korotokoff's sound is extinguished) is defined as the lowest blood pressure. By measuring blood flow velocity by the measuring portion 101, the highest and the lowest blood pressures are measured and also a value of blood rheology is measured.

By measuring and assessing blood rheology simultaneously with measuring blood pressure, also pressure at that occasion can accurately be grasped and simultaneously with measuring blood pressure, an error of blood rheology by an individual difference of blood pressure can be corrected further accurately.

Although according to the embodiment, blood rheology is measured simultaneously with measuring blood pressure by the blood pressure meter, the apparatus can also be used as a pulse meter by measuring a temporal interval between peaks of the waveform of FIG. 1. Further, it is also possible to arrange the cuff at the finger tip and utilizing blood pressure at a vicinity of the capillary at the finger tip.

Embodiment 13

Figure 26:
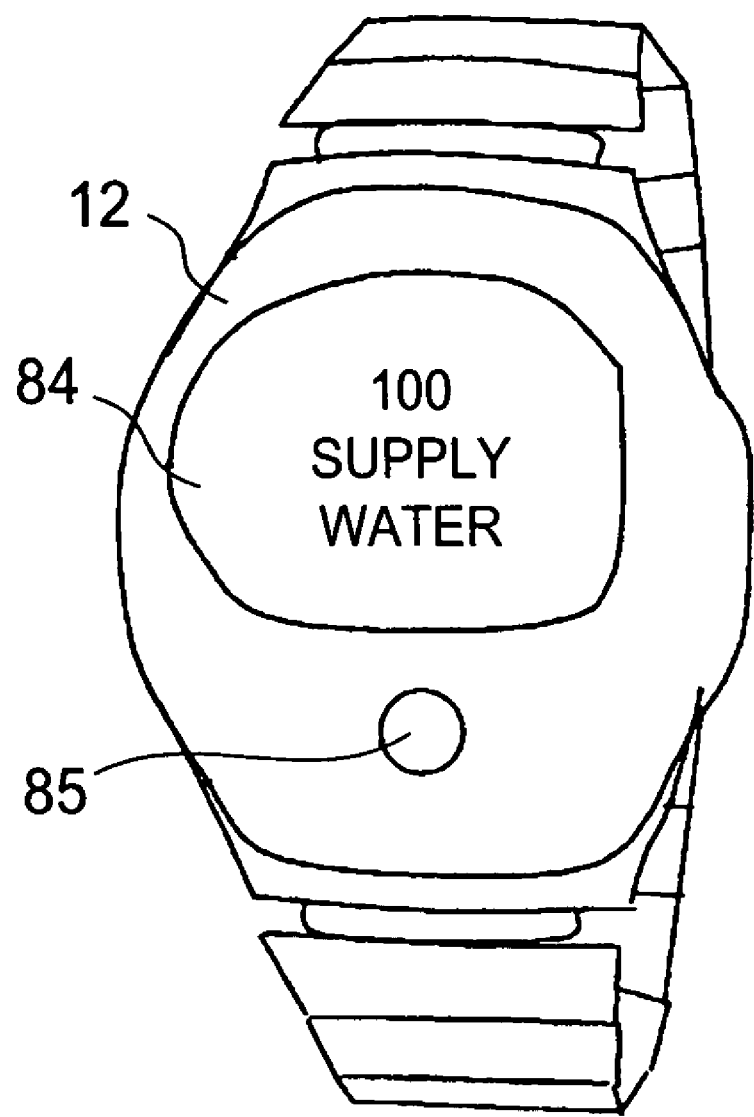
FIG. 26 illustrates a thirteenth embodiment of the invention.

FIG. 26 is an explanatory view showing a constitution providing the measuring portion at the finger tip (not illustrated) in the blood rheology measuring apparatus according to Embodiment 4. When a state of high blood rheology (high viscosity) is chronically continued, there is a high possibility of falling into an extremely dangerous health state such as arterial sclerosis.

Therefore, blood rheology is always measured and when the state of high blood rheology (high viscosity) is maintained or when blood rheology becomes equal to or lower than a predetermined value, by alarming a user by a detecting portion 85 of LED or the like, displaying to urge to supply water, improvement of life (insufficient sleep or the like) at a display portion 84, the above-described state can be avoided.

Embodiment 14

Figure 27:
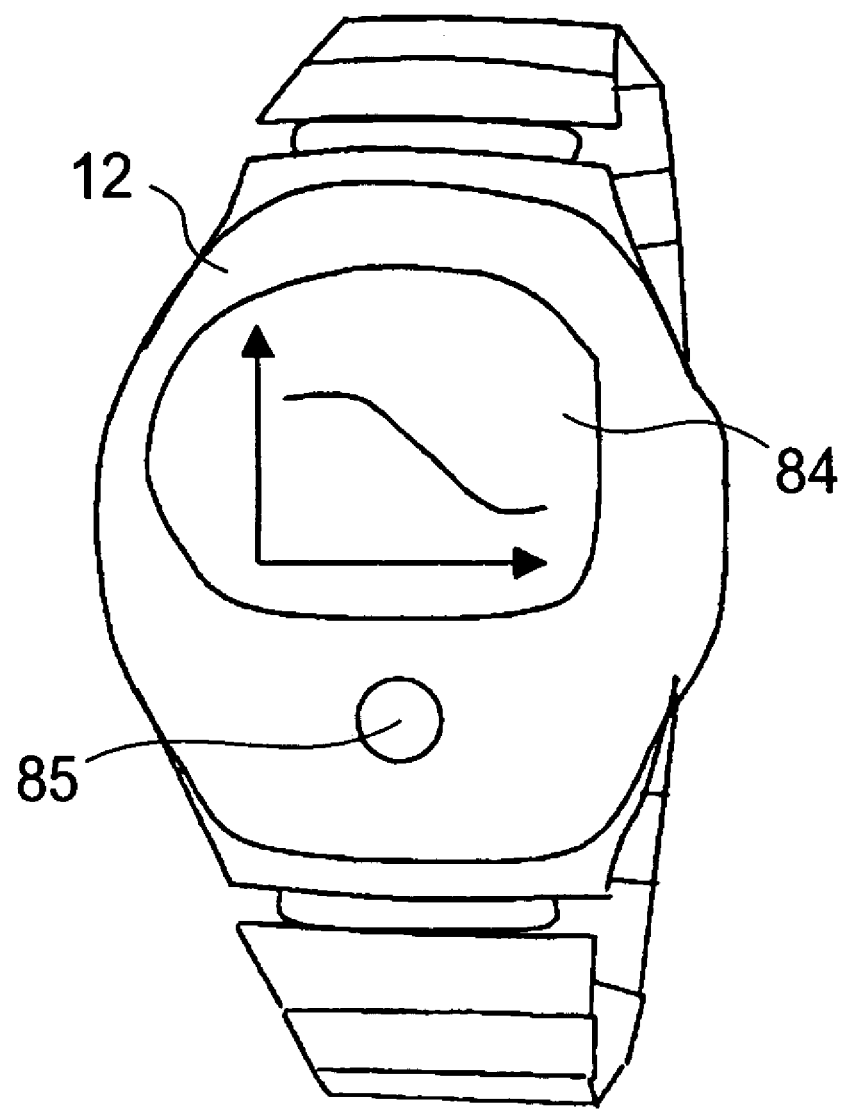
FIG. 27 illustrates a fourteenth embodiment of the invention.

FIG. 27 is an explanatory view showing a constitution providing the measuring portion at the finger tip (not illustrated) in the blood rheology measuring apparatus according to Embodiment 4. FIG. 27 is an explanatory view showing a state of displaying a daily trend of blood rheology at a display portion 84. The blood rheology is changed by daily life such as sleep time period, eating habit, presence or absence of exercise or the like and by observing a change in the blood rheology, it can be determined whether life of the subject is healthy, which can amount to prevention of disease of the circulatory system such as arterial sclerosis.

Blood rheology is changed daily and it is difficult to determine the health state of the subject by only measuring blood rheology once. Therefore, for example, when blood rheology before meal and blood rheology after meal are measured for a week, the health state of the subject can be grasped further accurately. Further, there can also be confirmed an effect in the case of continuously intaking food for improving blood rheology, for example, fermented soybeans, black vinegar, tomato juice, vegetable juice or the like.

Figure 28:
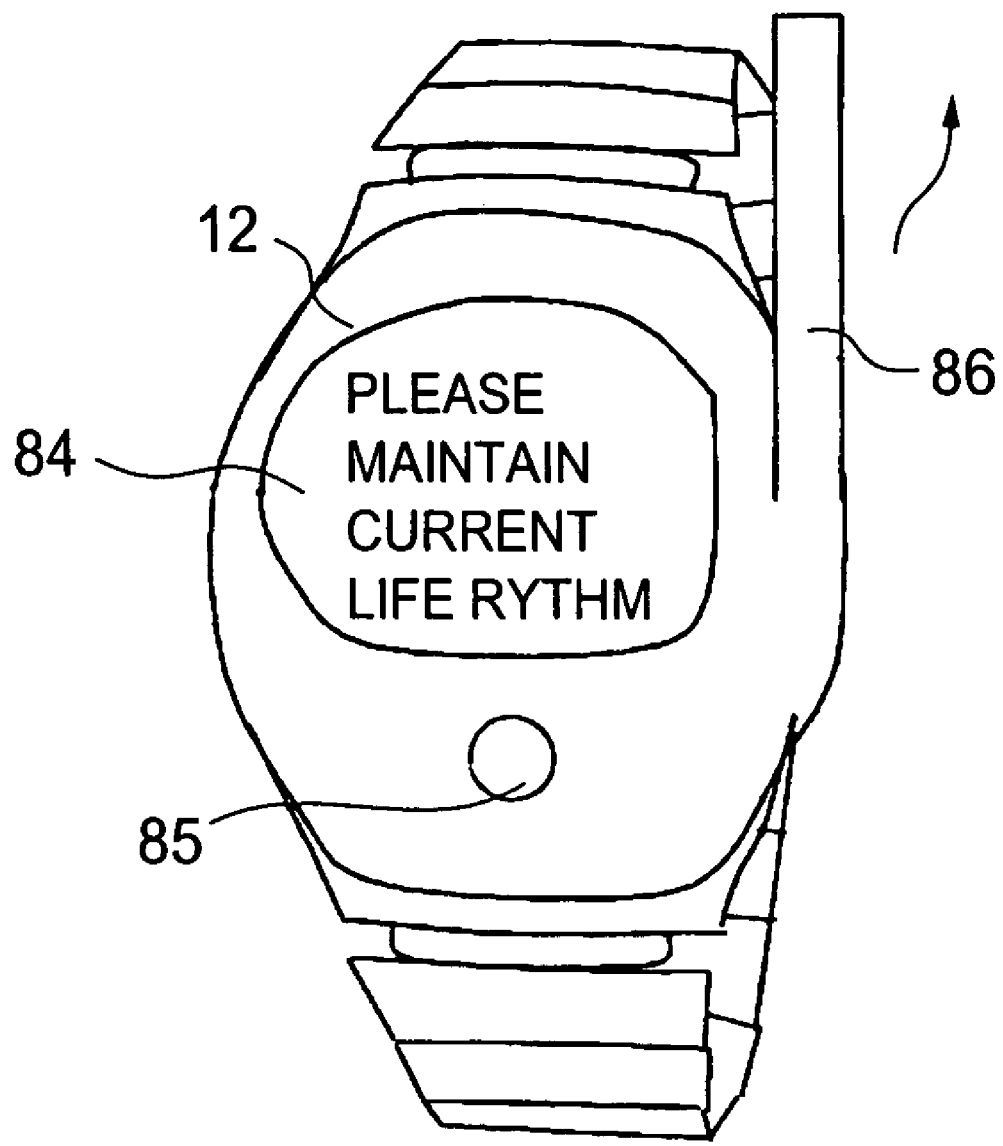
FIG. 28 illustrates a fifteenth embodiment of the invention.

FIG. 28 is an explanatory view showing a behavior of transmitting a measured value of blood rheology to a terminal by way of wireless, determining the health state of the subject based on the data and transferring a result of diagnosis. In FIG. 28, a terminal at a destination of transfer is omitted. Numeral 86 designates an antenna. Since a change in a value of blood rheology is small or the value is changed by measuring time or physical condition and therefore, by transferring measured data to the terminal, diagnosing the data by a specialist such as medical doctor and returning advice with regard to life to the user (advice with regard to food for improving blood rheology, advice with regard to sleep time or exercise time) a concern of erroneously recognizing the health state can be avoided and a state of blood rheology of the subject can be assessed and accordingly, the health state of the subject can be assessed and diagnosed further accurately.

The blood rheology measuring apparatus according to the invention comprises means for detecting the flow velocity of the blood flowing in the blood vessel in the mode of the Doppler shift signal by transmitting and receiving the wave from the face of the skin and means for analyzing blood rheology from the temporal change of the flow velocity value of the blood detected by the means and therefore, small-sized formation of the apparatus can be realized and since the measurement is carried out noninvasively, blood rheology can be measured simply at any time at anywhere even at outside of a medical institution without applying burden on a subject.

Further, according to the blood rheology measuring apparatus of the invention for analyzing blood rheology from the temporal change of the flow velocity value of the blood by dividing the maximum blood flow velocity of one pulse by the integrated value of the pulse velocity, although the measured blood flow velocity is not dependent only on blood rheology but dependent on a condition of thickness of the blood vessel, the wall quality or the blood pressure, when the correction amount in correspondence with the absolute value is provided by carrying out the correction by measurements by the conventional method capable of carrying out absolute measurement by comparing with the reference of physiological salt water or the like and the method of the invention in parallel, blood rheology can absolutely be measured by the apparatus.

According to the blood rheology measuring apparatus comprising means for detecting a flow velocity of the blood flowing in the blood vessel in a mode of a Doppler shift signal by transmitting and receiving a wave from a face of the skin, means for calculating an intensity of each of frequency components of the Doppler shift signal (histogram), means for extracting a maximum frequency in a signal of an intensity level equal to or larger than a threshold in the histogram, or a maximum frequency when an integrated value from a low frequency component reaches a predetermined rate of a total thereof in the histogram and means for providing a temporal change waveform of the extracted frequency (frequency waveform) and the blood rheology measuring apparatus of the invention, wherein a blood rheology is analyzed by an area value of a portion at and above a line connecting a minimum value of one pulse waveform and a minimum value of a successive pulse waveform of the frequency waveform, small-sized formation of the apparatus can be realized, since the measurement can be carried out noninvasively, blood rheology can be measured simply at any time at anywhere even at outside of a medical institution without applying burden on a subject and further, it is not necessary to provide the correction amount in correspondence with the absolute value by carrying out the correction of the measurements of the conventional method and the method of the invention in parallel and blood rheology can directly be measured absolutely by the apparatus.

According to the blood rheology measuring apparatus of the invention adopting an ultrasonic wave transmitter and receiver for transmitting and receiving an ultrasonic wave to and from the artery at the finger tip portion as means for detecting the flow velocity of the blood flowing in the blood vessel or an ultrasonic wave transmitter and receiver for transmitting and receiving an ultrasonic wave to and from the artery of the finger portion, since the measured portion is the finger, the blood flow velocity measuring portion can be downsized.

Further, according to the blood rheology measuring apparatus of the invention, by providing means for detecting temperature of the blood vessel portion and means for operating and compensating for an amount of a change in the f low velocity of the blood based on expansion and contraction of the blood vessel by a temperature value detected by the means, blood rheology can be measured accurately.

Further, according to the blood rheology measuring apparatus of the invention, by providing blood pressure measuring means and means for operating and compensating for an amount of a change based on blood pressure by dividing by a blood pressure value detected by the means, blood rheology can be measured accurately.

According to the invention, a structure of a holding portion is constituted by a structure in which the finger ring is constituted by a shape capable of identifying an upper side and a lower side of a cut face when the finger ring is cut by a face orthogonal to an axial direction thereof and the measuring portion is arranged at a position of 10 degrees through 80 degrees when a vertical lower direction is defined as 0 degree centering on an axis of the cylinder. Thereby, an ultrasonic wave can be made to be incident to accurately aim at the artery and an accuracy of measuring the flow velocity of the blood can be promoted and accordingly, blood rheology can accurately be assessed.

Further, according to the invention, the blood rheology measuring apparatus is integrated with a sensor portion at an inner peripheral portion of the finger ring to be brought into contact with the finger and the sensor portion is always carried along with the signal processing portion of the ultrasonic wave to be able to measure blood rheology and therefore, a change in blood rheology in life of one day can be assessed as continuous change, which can amount to prevention of disease of the circulatory system (myocardial infarction or the like).

Further, according to the invention, by integrating the measuring portion in the blood rheology measuring apparatus to a cuff, not only blood rheology can be measured simultaneously with measuring blood pressure but also by correcting blood rheology by a provided blood pressure value, further accurate blood rheology information can be provided which can amount to prevention of disease of the circulatory system.

What is claimed is:

1. A blood rheology measuring apparatus comprising:
a measuring portion for measuring a flow velocity of the blood flowing in a blood vessel of a person in a mode of a Doppler shift signal by transmitting and receiving a wave to and from a surface of the person's skin; and
an information processing portion having means for calculating an intensity at each of frequency components of the Doppler shift signal, means for extracting a maximum frequency in a signal at an intensity level equal to or larger than a threshold in the histogram or a maximum frequency when an integrated value from a low frequency component reaches a predetermined rate of a total thereof in the histogram, and means for providing a temporal change waveform of the extracted frequency;
wherein a blood rheology is analyzed by an area value of a portion at and above a line connecting a minimum value of one pulse waveform and a minimum value of a successive pulse waveform of the frequency waveform.

2. A blood rheology measuring apparatus according to claim 1; wherein the measuring portion comprises an ultrasonic wave transmitter and receiver for transmitting and receiving an ultrasonic wave to and from an artery at a tip portion of the person's finger.

3. A blood rheology measuring apparatus according to claim 1; wherein the measuring portion comprises an ultrasonic wave transmitter and receiver for transmitting and receiving an ultrasonic wave to and from an artery at the person's finger.

4. A blood rheology measuring apparatus according to claim 1; further comprising a temperature measuring portion for measuring a temperature of the blood vessel used for detecting the flow velocity of blood; and wherein the information processing portion has means for operating and compensating for an amount of changing the flow velocity of the blood based on expansion and contraction of the blood vessel by a value of the temperature measured by the temperature measuring portion.

5. A blood rheology measuring apparatus according to claim 1; further comprising blood pressure measuring means for measuring a blood pressure of the person; wherein the information processing portion has means for operating and compensating for a change amount based on a blood pressure by dividing by a value of the blood pressure measured by the blood pressure measuring means.

6. A blood rheology measuring apparatus according to claim 1; further comprising a blood pressure measuring portion for measuring the person's maximum blood pressure; and wherein the information processing portion has means for operating and compensating for a change amount based on a blood pressure by dividing the maximum frequency in the frequency waveform by a value of the maximum blood pressure measured by the blood pressure measuring portion.

7. A blood rheology measuring apparatus according to claim 1; wherein the measuring portion and the information processing portion are integrally or individually made portable to thereby enable the information concerning the blood rheology to be obtained continuously or daily.

8. A blood rheology measuring apparatus according to claim 1; further comprising a data inputting portion for inputting individual information of a person to be measured.

9. A blood rheology measuring apparatus according to claim 1; wherein life habit information suitable for a person to be measured is informed to a subject based on information concerning the blood rheology of the person to be measured.

10. A blood rheology measuring apparatus according to claim 1; further comprising a data holding portion for storing the information concerning the measured blood rheology to enable a daily change in the blood rheology of the person to be measured to be assessed from data stored to the data holding portion.

11. A blood rheology measuring apparatus according to claim 1; further comprising a pressure measuring portion.

12. A blood rheology measuring apparatus according to claim 1; further comprising a cuff; a mechanism for adjusting a pressure of fastening the cuff; and a pressure measuring portion for measuring the pressure.

13. A blood rheology measuring apparatus according to claim 12; wherein the information concerning the blood rheology provided by the pressure measuring portion is operated and corrected.

14. A blood rheology measuring apparatus according to claim 1; further comprising a data inputting portion for inputting individual information of a person to be measured, the individual information being information about a food.

15. A blood rheology measuring apparatus according to claim 1; wherein the measuring portion measures the information by a predetermined timing and when a predetermined value of the blood rheology is reached, the value is detected by the person to be measured.

16. A blood rheology measuring apparatus according to claim 1; further comprising a temperature measuring portion for measuring a temperature inside of the person's body or a surface of the person's body at a vicinity of the measuring portion.

17. A blood rheology measuring apparatus according to claim 1; further comprising a temperature elevating portion for elevating the temperature inside of the persons's body or the surface of the person's body at the vicinity of the measuring portion.

18. A blood rheology measuring apparatus according to claim 17; wherein the temperature elevating portion is the same as the measuring portion.

19. A blood rheology measuring apparatus according to claim 1; wherein the measuring portion is held by a holding structure capable of holding the measuring portion by bringing the measuring portion into contact with the surface of the person's body.

20. A blood rheology measuring apparatus according to claim 19; wherein the holding structure is a member having an insulating property.

21. A blood rheology measuring apparatus according to claim 19; wherein the holding structure is a member having an elasticity of a rubber.

22. A blood rheology measuring apparatus according to claim 19; wherein the holding structure has a shape of a cylindrical finger ring, and the measuring portion is integrated to an inner peripheral portion of the finger ring to be brought into contact with the living body.

23. A blood rheology measuring apparatus according to claim 22; wherein the measuring portion is integrated to the inner peripheral portion of the finger ring to be brought into contact with the living body by being shifted to either of a right side or a left side from a portion of the belly of the finger.

24. A blood rheology measuring apparatus according to claim 22; wherein the temperature measuring portion is integrated to the inner peripheral portion of the finger ring to be brought into contact with the living, body by being shifted to either of a right side or a left side from a portion of the belly of the finger.

25. A blood rheology measuring apparatus according to claim 19; wherein the holding structure has a shape of a cylindrical finger ring capable of identifying an upper side and a lower side of a cut face when the finger ring is cut by a face orthogonal to an axial direction thereof, and the measuring portion is disposed at a position of 10 degrees through 80 degrees when a lower direction of the cut face is defined as 0 degree centering on an axis of the cylinder.

26. A blood rheology measuring apparatus according to claim 1; wherein the measuring portion measures a change in a blood flow velocity at a capillary of a finger tip.

* * * * *